United States Patent
Grudem et al.

(10) Patent No.: US 7,422,602 B2
(45) Date of Patent: Sep. 9, 2008

(54) MEDICAL GRAFTING METHODS AND APPARATUS

(75) Inventors: Jerry Grudem, St. Louis Park, MN (US); William J Swanson, St. Paul, MN (US); Todd A Berg, Plymouth, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 469 days.

(21) Appl. No.: 11/144,209

(22) Filed: Jun. 2, 2005

(65) Prior Publication Data

US 2005/0240204 A1    Oct. 27, 2005

Related U.S. Application Data

(62) Division of application No. 10/309,387, filed on Dec. 2, 2002, now Pat. No. 6,960,219, which is a division of application No. 09/920,541, filed on Aug. 1, 2001, now Pat. No. 6,511,491, which is a division of application No. 09/324,997, filed on Jun. 2, 1999, now abandoned.

(60) Provisional application No. 60/123,482, filed on Mar. 9, 1999.

(51) Int. Cl.
  *A61F 2/06* (2006.01)
(52) U.S. Cl. ........................ 623/1.36; 623/903; 606/153
(58) Field of Classification Search ....... 623/1.11–1.15; 606/194

See application file for complete search history.

(56) References Cited

U.S. PATENT DOCUMENTS

| | | | |
|---|---|---|---|
| 3,903,892 A | 9/1975 | Komiya | |
| 4,214,587 A | 7/1980 | Sakura, Jr. | |
| 4,418,693 A | 12/1983 | LeVeen | |
| 4,459,252 A | 7/1984 | MacGregor | |
| 4,503,569 A | 3/1985 | Dotter | |
| 4,589,295 A * | 5/1986 | Jerry et al. | 74/360 |
| 4,592,754 A | 6/1986 | Gupte et al. | |
| 4,605,406 A | 8/1986 | Cahalan et al. | |
| 4,617,932 A | 10/1986 | Kornberg | |
| 4,629,458 A | 12/1986 | Pinchuk | |
| 4,632,842 A | 12/1986 | Karwoski et al. | |
| 4,651,733 A | 3/1987 | Mobin-Uddin | |
| 4,665,906 A | 5/1987 | Jervis | |
| 4,665,918 A | 5/1987 | Garza et al. | |
| 4,705,517 A | 11/1987 | DiPisa, Jr. | |
| 4,718,907 A | 1/1988 | Karwoski et al. | |

(Continued)

FOREIGN PATENT DOCUMENTS

AU    670239    1/1994

(Continued)

*Primary Examiner*—Suzette J Gherbi
(74) *Attorney, Agent, or Firm*—Ropes & Gray LLP

(57) ABSTRACT

Methods and apparatus for making an anastomotic connection between first and second tubular fluid conduits are provided. For example, a connector may be configured for attachment to the first and second tubular fluid conduits and have an interior thereof substantially accessible to the interior of the first tubular fluid conduit. The connector may be configured for annular enlargement. An expandable structure is provided having a first portion configured to annularly enlarge the connector by engaging the interior of the connector. A second portion may be configured to extend through an opening in the medial portion of the first tubular fluid conduit.

9 Claims, 25 Drawing Sheets

U.S. PATENT DOCUMENTS

| | | |
|---|---|---|
| 4,733,665 A | 3/1988 | Palmaz |
| 4,738,740 A | 4/1988 | Pinchuk et al. |
| 4,739,762 A | 4/1988 | Palmaz |
| 4,743,252 A | 5/1988 | Martin, Jr. et al. |
| 4,748,984 A | 6/1988 | Patel |
| 4,787,899 A | 11/1988 | Lazarus |
| 4,795,458 A | 1/1989 | Regan |
| 4,798,606 A | 1/1989 | Pinchuk |
| 4,892,539 A | 1/1990 | Koch |
| 4,909,258 A | 3/1990 | Kuntz et al. |
| 4,969,890 A | 11/1990 | Sugita et al. |
| 5,035,702 A | 7/1991 | Taheri |
| 5,037,377 A | 8/1991 | Alonso |
| 5,061,245 A | 10/1991 | Waldvogel |
| 5,061,275 A | 10/1991 | Wallsten et al. |
| 5,084,065 A | 1/1992 | Weldon et al. |
| 5,104,399 A | 4/1992 | Lazarus |
| 5,116,360 A | 5/1992 | Pinchuk et al. |
| 5,122,154 A | 6/1992 | Rhodes |
| 5,135,467 A | 8/1992 | Citron |
| 5,147,370 A | 9/1992 | McNamara et al. |
| 5,163,951 A | 11/1992 | Pinchuk et al. |
| 5,171,233 A | 12/1992 | Amplatz et al. |
| 5,201,901 A | 4/1993 | Harada et al. |
| 5,207,695 A | 5/1993 | Trout |
| 5,209,731 A | 5/1993 | Sterman et al. |
| 5,211,658 A | 5/1993 | Clouse |
| 5,211,683 A | 5/1993 | Maginot |
| 5,226,429 A | 7/1993 | Kuzmak |
| 5,234,447 A | 8/1993 | Kaster et al. |
| 5,256,150 A | 10/1993 | Quiachon et al. |
| 5,275,622 A | 1/1994 | Lazarus et al. |
| 5,287,861 A | 2/1994 | Wilk |
| 5,297,564 A | 3/1994 | Love |
| 5,304,220 A | 4/1994 | Maginot |
| 5,306,240 A | 4/1994 | Berry |
| 5,316,023 A | 5/1994 | Palmaz et al. |
| 5,334,217 A | 8/1994 | Das |
| 5,354,309 A | 10/1994 | Schnepp-Pesch et al. |
| 5,354,336 A | 10/1994 | Kelman et al. |
| 5,360,443 A * | 11/1994 | Barone et al. ............... 623/1.13 |
| 5,366,504 A | 11/1994 | Andersen et al. |
| 5,387,235 A | 2/1995 | Chuter |
| 5,395,349 A | 3/1995 | Quiachon et al. |
| 5,397,345 A | 3/1995 | Lazarus |
| 5,397,355 A | 3/1995 | Marin et al. |
| 5,409,019 A | 4/1995 | Wilk |
| 5,419,324 A | 5/1995 | Dillow |
| 5,425,765 A | 6/1995 | Tiefenbrun et al. |
| 5,429,144 A | 7/1995 | Wilk |
| 5,433,727 A | 7/1995 | Sideris |
| 5,437,288 A | 8/1995 | Schwartz et al. |
| 5,443,497 A | 8/1995 | Venbrux |
| 5,443,499 A | 8/1995 | Schmitt |
| 5,452,733 A | 9/1995 | Sterman et al. |
| 5,456,712 A | 10/1995 | Maginot |
| 5,480,423 A | 1/1996 | Ravenscroft et al. |
| 5,484,418 A | 1/1996 | Quiachon et al. |
| 5,489,295 A | 2/1996 | Piplani et al. |
| 5,496,364 A | 3/1996 | Schmitt |
| 5,496,365 A | 3/1996 | Sgro |
| 5,507,769 A | 4/1996 | Marin et al. |
| 5,509,931 A | 4/1996 | Schmitt |
| 5,522,834 A | 6/1996 | Fonger et al. |
| 5,522,880 A | 6/1996 | Barone et al. |
| 5,522,882 A | 6/1996 | Gaterud et al. |
| 5,542,944 A | 8/1996 | Bhatta |
| 5,545,214 A | 8/1996 | Stevens |
| 5,549,663 A | 8/1996 | Cottone |
| 5,554,152 A | 9/1996 | Aita et al. |
| 5,562,725 A | 10/1996 | Schmitt et al. |
| 5,562,728 A | 10/1996 | Lazarus et al. |
| 5,571,172 A | 11/1996 | Chin |
| 5,584,875 A | 12/1996 | Duhamel et al. |
| 5,591,226 A | 1/1997 | Trerotola et al. |
| 5,617,878 A | 4/1997 | Taheri |
| 5,628,788 A | 5/1997 | Pinchuk |
| 5,632,772 A | 5/1997 | Alcime et al. |
| 5,653,747 A | 8/1997 | Dereume |
| 5,676,670 A | 10/1997 | Kim |
| 5,695,504 A | 12/1997 | Gifford, III et al. |
| 5,797,920 A | 8/1998 | Kim |
| 5,800,526 A | 9/1998 | Anderson et al. |
| 5,830,222 A | 11/1998 | Makower |
| 5,843,164 A | 12/1998 | Frantzen et al. |
| 5,843,170 A | 12/1998 | Ahn |
| 5,843,175 A | 12/1998 | Frantzen |
| 5,941,908 A | 8/1999 | Goldsteen et al. |
| 5,976,178 A | 11/1999 | Goldsteen et al. |
| 5,989,276 A * | 11/1999 | Houser et al. ............... 606/170 |
| 6,036,702 A | 3/2000 | Bachinski et al. |
| 6,113,612 A * | 9/2000 | Swanson et al. ............ 623/1.15 |
| 6,117,156 A * | 9/2000 | Richter et al. ............... 606/194 |
| 6,152,937 A | 11/2000 | Peterson et al. |
| 6,193,734 B1 | 2/2001 | Bolduc et al. |
| 6,391,036 B1 | 5/2002 | Berg et al. |
| 6,428,550 B1 | 8/2002 | Vargas et al. |
| 6,428,565 B1 | 8/2002 | Wisselink |
| 6,440,163 B1 | 8/2002 | Swanson et al. |
| 6,451,048 B1 | 9/2002 | Berg et al. |
| 6,511,491 B2 | 1/2003 | Grudem et al. |
| 6,602,263 B1 * | 8/2003 | Swanson et al. ............ 606/153 |
| 6,620,176 B1 | 9/2003 | Peterson et al. |
| 6,848,448 B1 * | 2/2005 | St. Germain et al. ........ 128/898 |
| 6,960,219 B2 * | 11/2005 | Grudem et al. ............. 606/153 |

FOREIGN PATENT DOCUMENTS

| | | |
|---|---|---|
| DE | 28 22 603 A | 11/1979 |
| DE | 4404806 | 2/1995 |
| DE | 195 42 733 A | 7/1997 |
| DE | 29713335 | 10/1997 |
| EP | 0 539 237 | 4/1993 |
| EP | 0 541 063 A | 5/1993 |
| EP | 0 541 063 A2 | 12/1993 |
| EP | 0 541 063 A3 | 12/1993 |
| EP | 637454 | 2/1995 |
| EP | 0 680 734 | 11/1995 |
| EP | 0 684 022 | 11/1995 |
| EP | 0 701 800 A1 | 3/1996 |
| EP | 0 712 614 A1 | 5/1996 |
| EP | 0 732 087 | 9/1996 |
| EP | 0 732 088 A2 | 9/1996 |
| EP | 0 732 089 A2 | 9/1996 |
| EP | 737 453 A2 | 10/1996 |
| GB | 489316 | 7/1938 |
| GB | 2269104 A | 2/1994 |
| WO | WO 89/08433 A1 | 9/1989 |
| WO | WO 93/00868 | 1/1993 |
| WO | WO 93/13712 A | 7/1993 |
| WO | WO 93/20757 A2 | 10/1993 |
| WO | WO 94/01056 A1 | 1/1994 |
| WO | WO 94/06372 | 3/1994 |
| WO | WO 95/17127 | 6/1995 |
| WO | WO 95/21592 A1 | 8/1995 |
| WO | WO 95/32757 A1 | 12/1995 |
| WO | WO 96/01591 | 1/1996 |
| WO | WO 96/01599 | 1/1996 |
| WO | WO 96/14808 A1 | 5/1996 |
| WO | WO 96/18361 | 6/1996 |
| WO | WO 96/22745 | 8/1996 |
| WO | WO 96/25897 A2 | 8/1996 |
| WO | WO 97/13463 | 4/1997 |
| WO | WO 97/13471 | 4/1997 |

| | | | | | | |
|---|---|---|---|---|---|---|
| WO | WO 97/27893 | | 8/1997 | WO | WO 98/19631 A1 | 5/1998 |
| WO | WO 97/27897 | | 8/1997 | WO | WO 98/19636 | 5/1998 |
| WO | WO 97/27898 | | 8/1997 | WO | WO 98/26732 A1 | 6/1998 |
| WO | WO 97/41779 | A | 11/1997 | WO | WO 98/27868 A | 7/1998 |
| WO | WO 98/01086 | | 1/1998 | WO | WO 98/38939 A1 | 9/1998 |
| WO | WO 98/02099 | | 1/1998 | WO | WO 98/38941 A1 | 9/1998 |
| WO | WO 98/03118 | | 1/1998 | WO | WO 98/38942 A1 | 9/1998 |
| WO | WO 98/07399 | | 2/1998 | WO | WO 98/42262 | 10/1998 |
| WO | WO 98/08456 | | 3/1998 | WO | WO 98/55027 A | 12/1998 |
| WO | WO 98/08462 | A2 | 3/1998 | WO | WO 99/07289 A | 2/1999 |
| WO | WO 98/16161 | | 4/1998 | WO | WO 99/38454 | 8/1999 |
| WO | WO 98/19629 | A2 | 5/1998 | | | |
| WO | WO 98/19629 | A3 | 5/1998 | * cited by examiner | | |

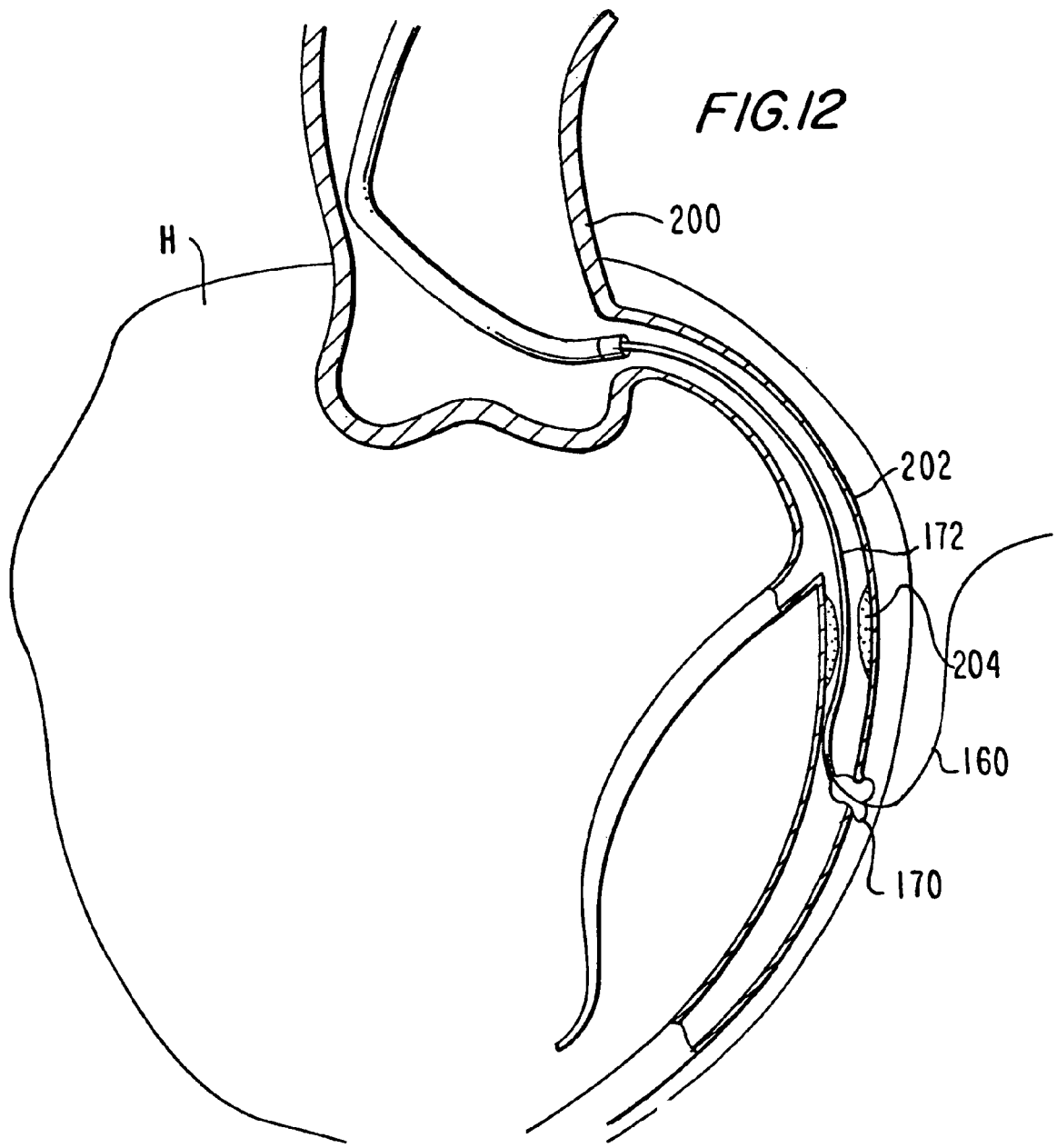
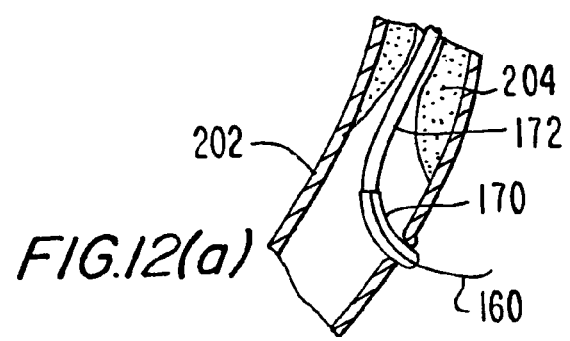

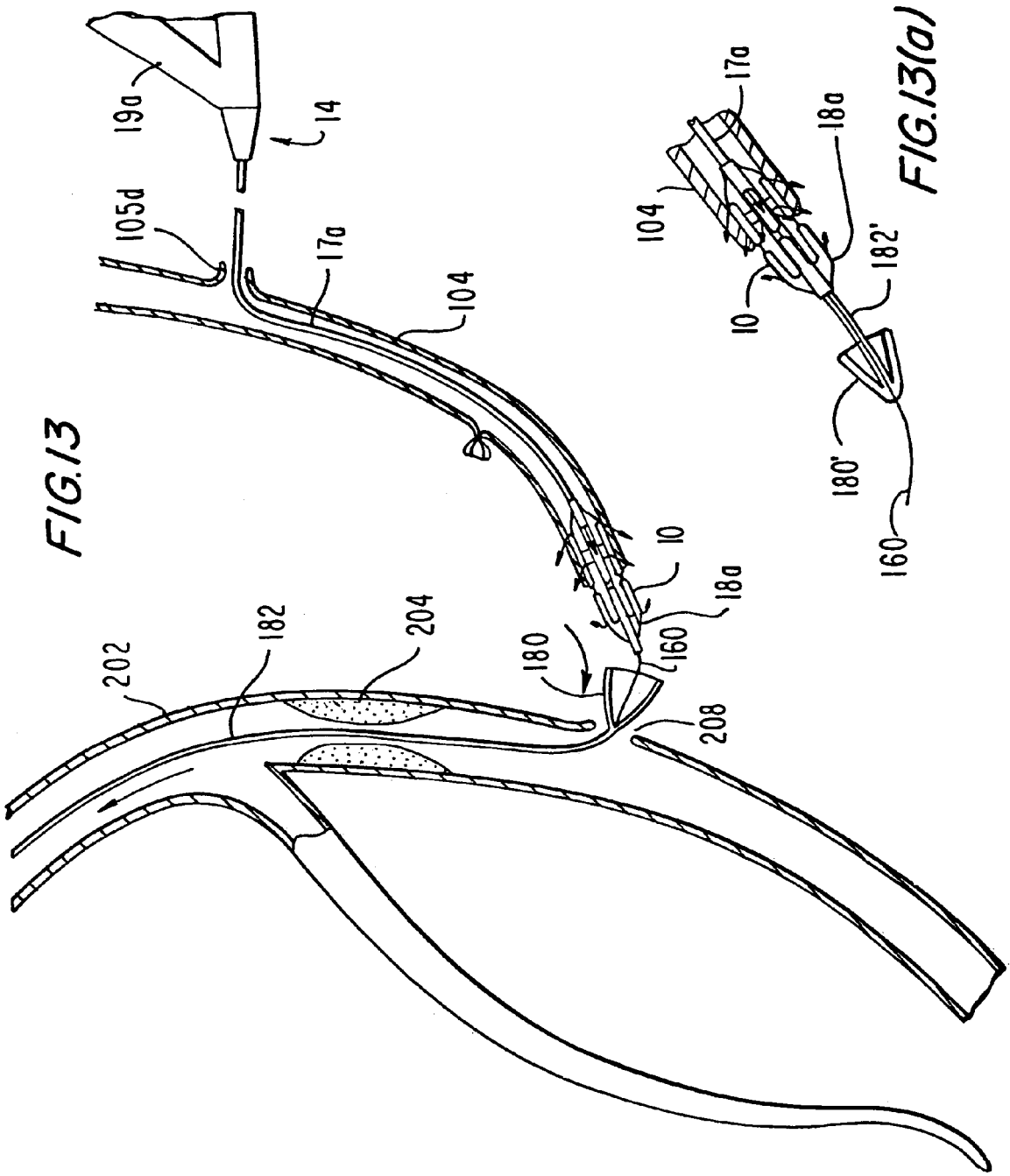

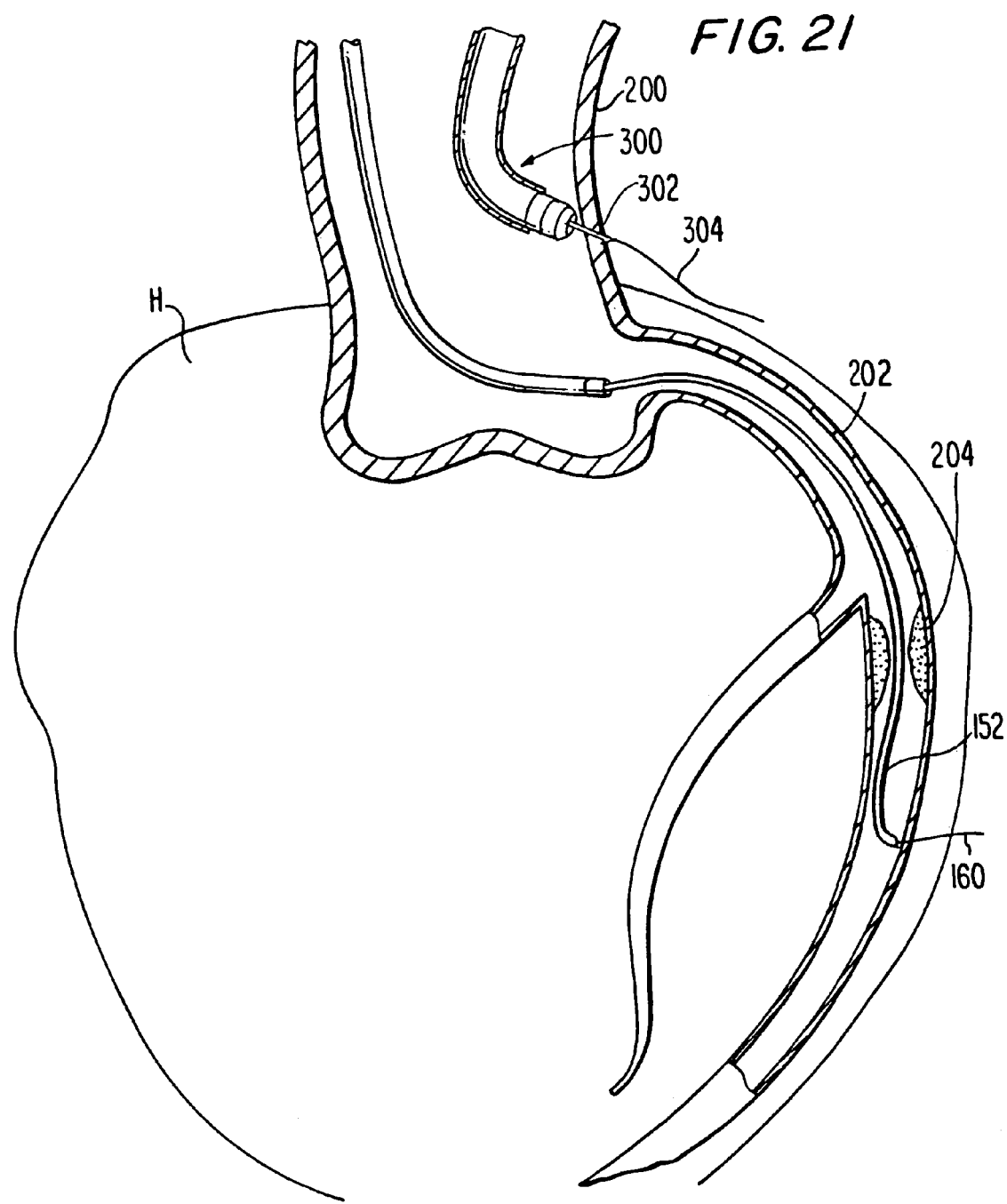

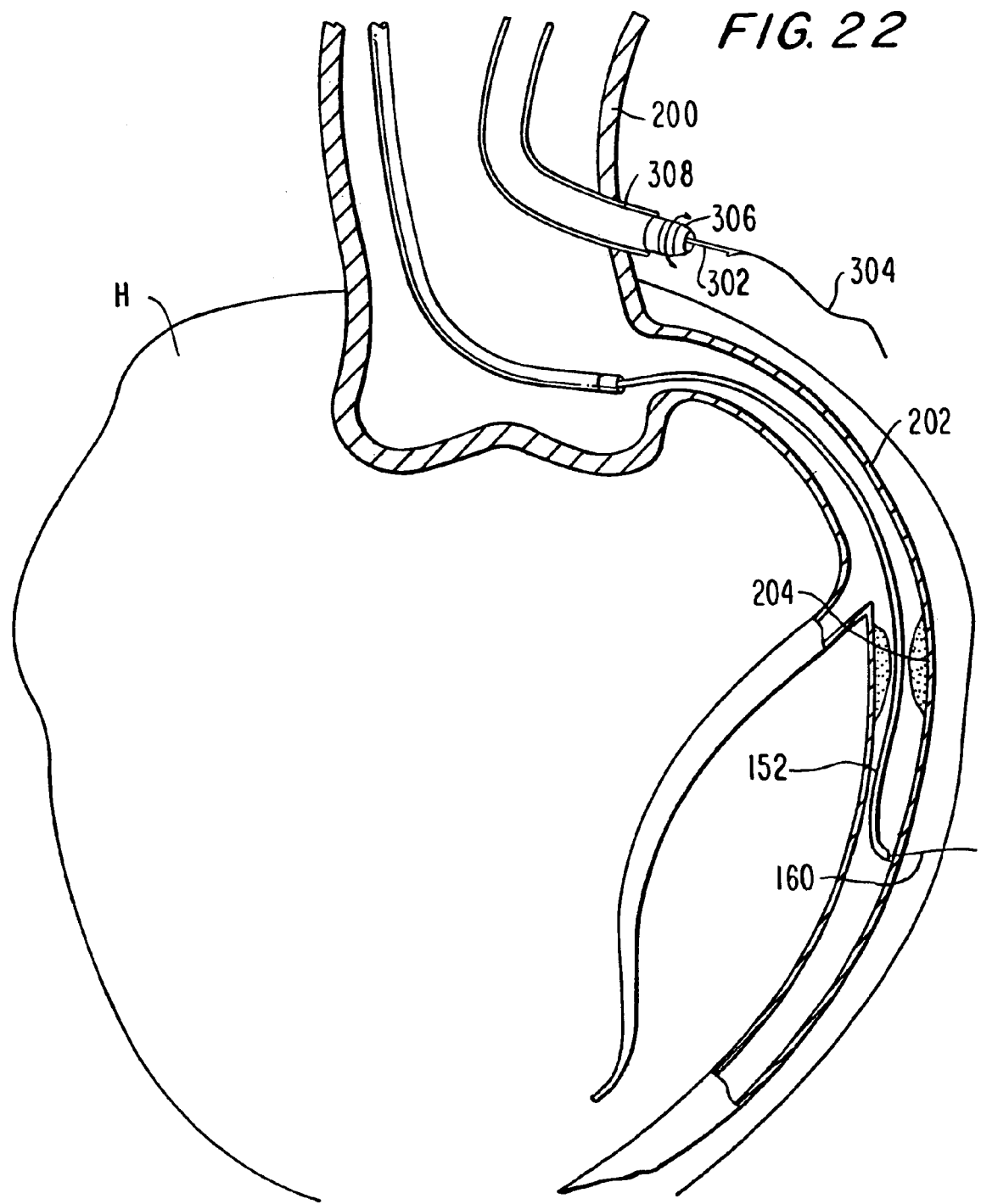

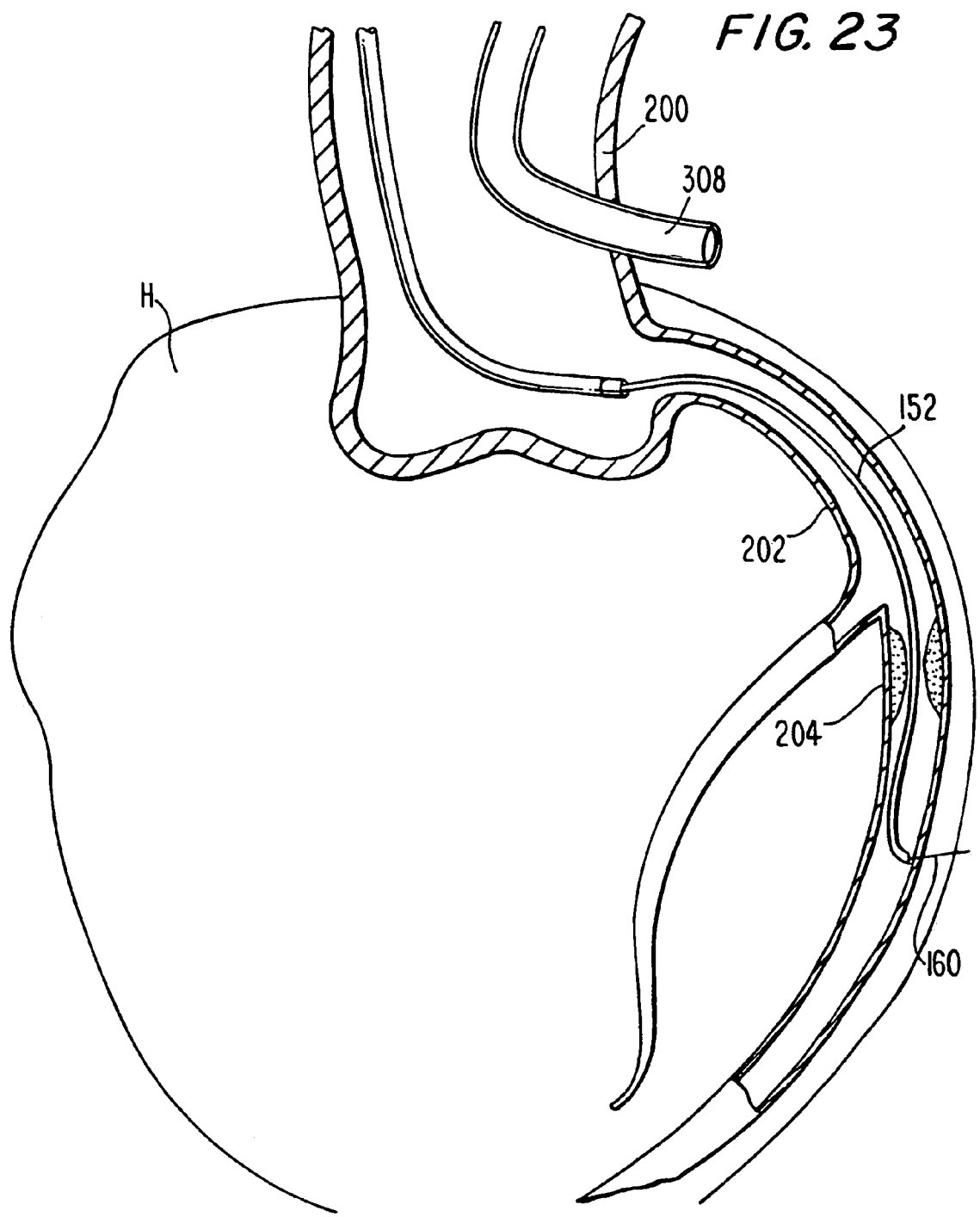

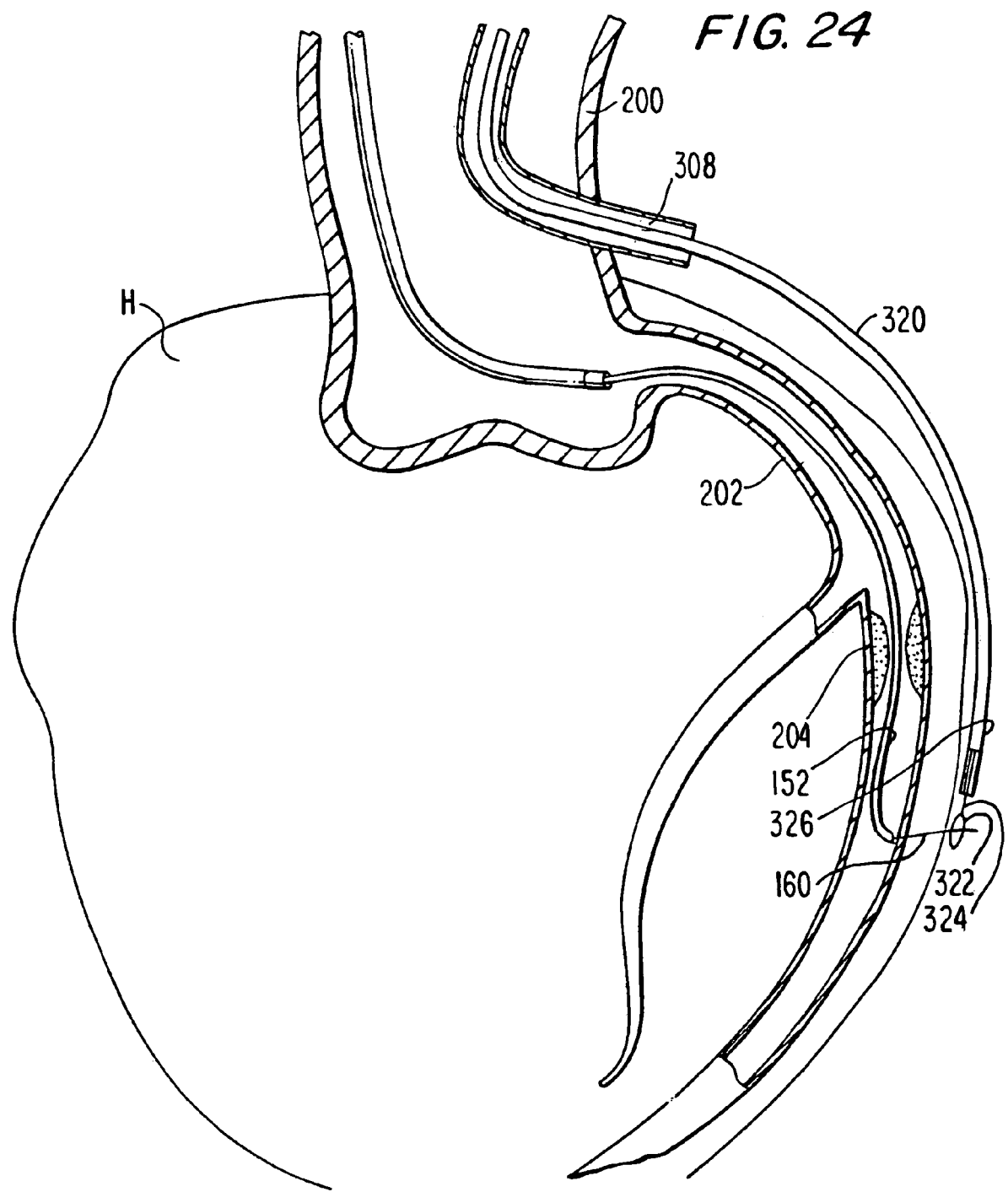

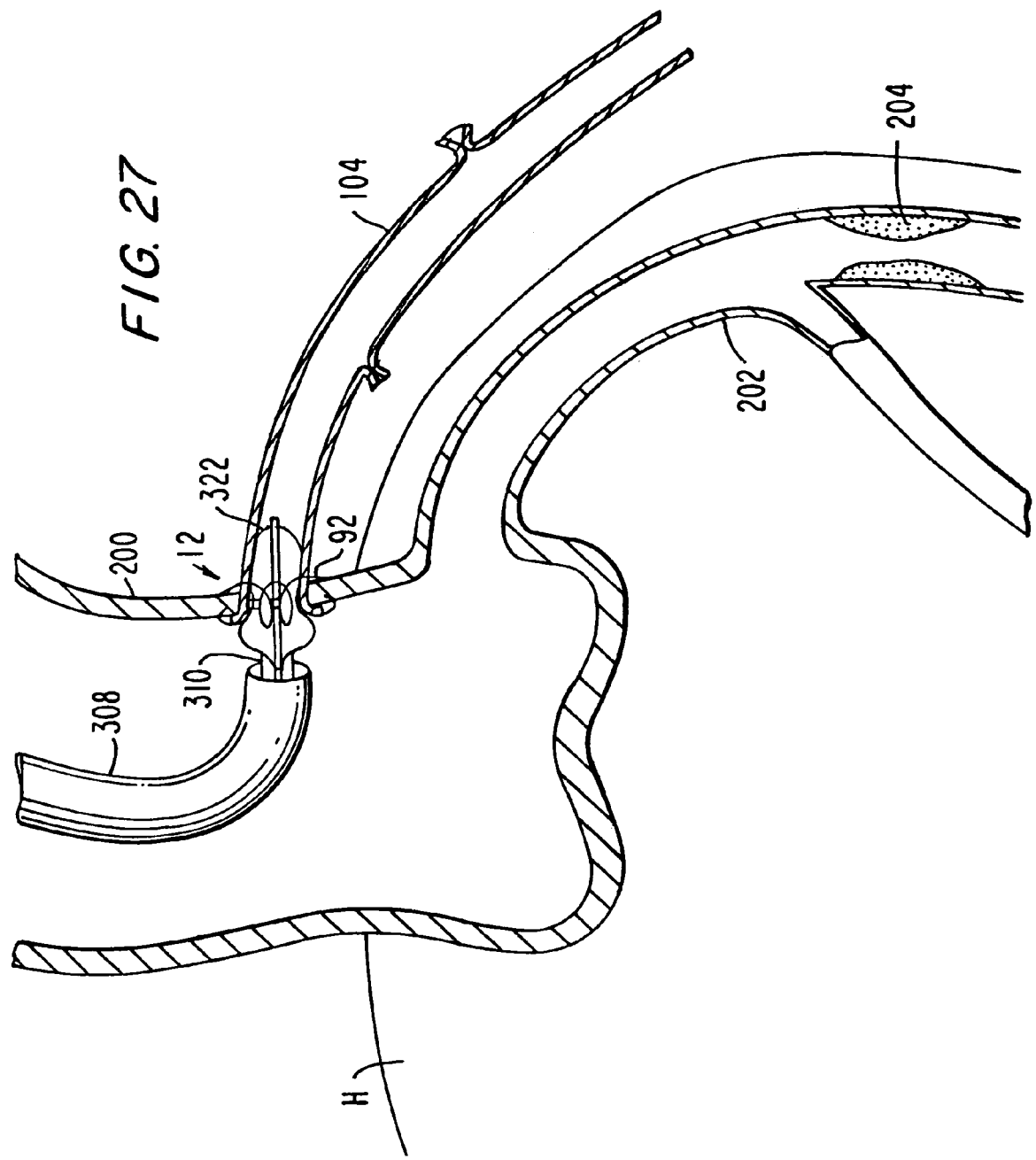

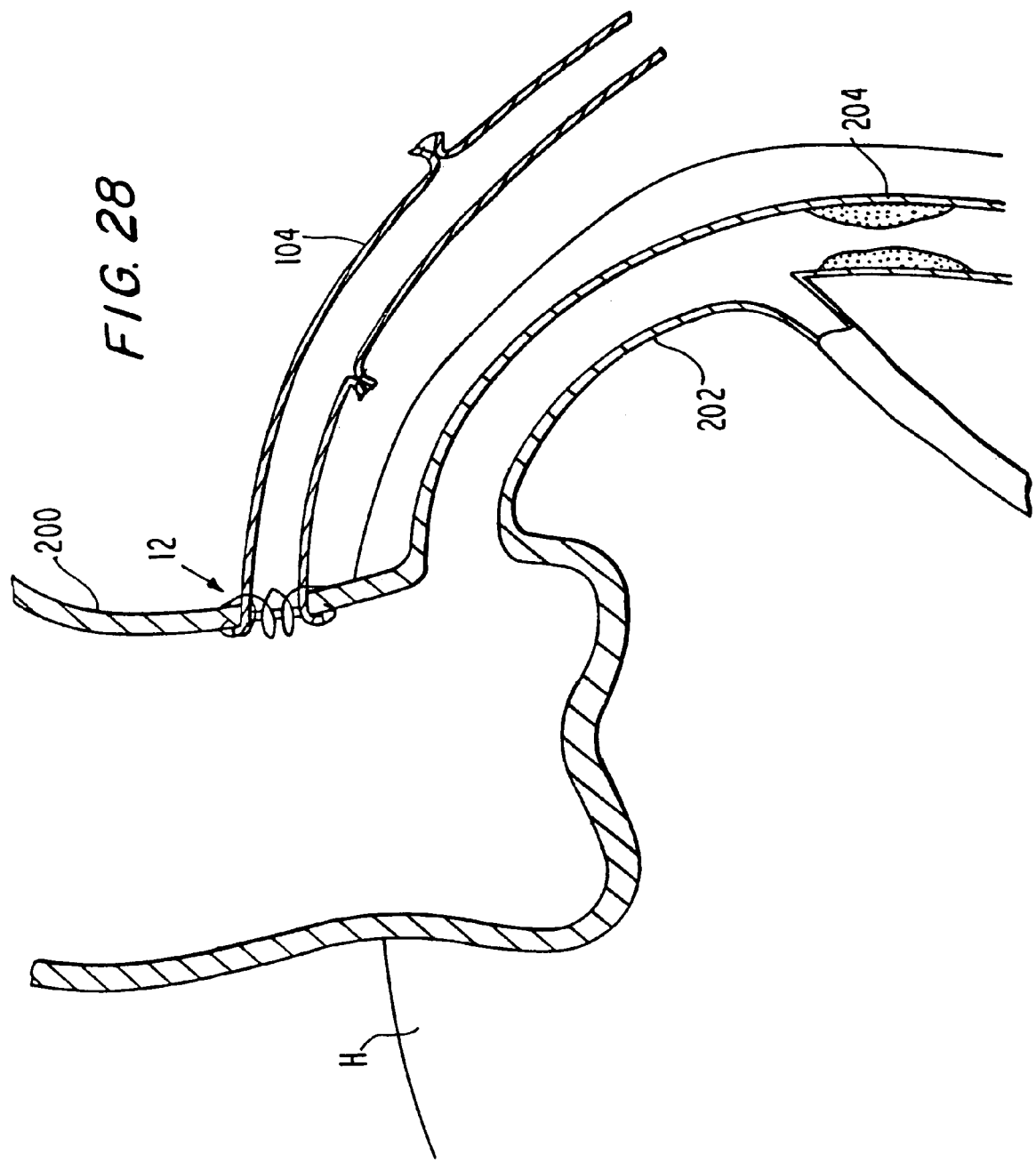

ature, e.g., a catheter-like structure, axially extending from an
MEDICAL GRAFTING METHODS AND APPARATUS This application is a division of U.S. patent application Ser. No. 10/309,387, filed Dec. 2, 2002, which is a divisional of U.S. patent application Ser. No. 09/920,541, filed Aug. 1, 2001, which is a division of U.S. patent application Ser. No. 09/324,997, filed Jun. 2, 1999 (now abandoned), which is a nonprovisional of U.S. provisional patent application No. 60/123,482, filed Mar. 9, 1999. All of these prior applications are hereby incorporated by reference herein in their entireties.

BACKGROUND OF THE INVENTION

This invention relates to medical methods and apparatus, and more particularly to methods and apparatus for installing a tubular graft in a patient for such purposes as bypassing an occlusion or narrowing in the patient's tubular body structure.

The invention is applicable to making anastomotic connections between all body conduits. For example, the invention also has application for attaching coronary artery bypass grafts. Specifically, connection methods and apparatus are provided for attaching the graft ends to the coronary artery and the aortic artery. In the case of the internal mammary artery, connection is required at the coronary artery only.

Conventional coronary artery bypass grafting requires the heart and associated vessels to be accessed through the center of the chest by splitting the sternum (e.g., median sternotomy) or through the side by separating the ribs (e.g., thoracotomy). The heart is typically stopped during this process, and the patient is placed on cardiopulmonary bypass. These procedural steps are typically performed in order to allow the physician to safely and precisely sew the grafts with sutures to the exposed arteries as deemed necessary. However, this procedure may involve risks to the patient attributable to the magnitude of the incision required and the procedure of stopping the heart, which allow the physician the access to stitch on a non-beating heart, i.e., "static" stitching. This procedure may also be associated with various complications, including stroke, heart block, and long patient recovery times. Another factor is the considerable operation time involved due to the criticality of individual hand sewing of each graft end required by the suture process. The precision with which the grafts are sewn may influence the ultimate patency term for the graft.

Typical prior art procedures have been described by Heartport, for example, which attempts to connect vessels through ports inserted between the ribs but also requires the heart to be stopped and the grafts be sewn in place. Cardiothoracic Systems describes a procedure wherein the heart is allowed to beat, but full access to the heart is required as well as hand sewing of the graft segments to the beating heart. Other procedures describe the use of robots and automated mechanical assist devices to complete a sewn anastomosis on beating hearts or through small incisions.

It is thus an advantage of the current invention to overcome some of these difficulties associated with cardiac surgery.

It is an advantage of the invention to eliminate the need to stop the heart.

It is a further advantage of the invention to reduce significantly the size of the incision and to reduce the exposure of the heart and aorta necessary to perform the surgery.

It is still a further advantage of the invention to reduce the time necessary to perform the anastomosis procedure by eliminating the time-consuming task of manually suturing the vessels together.

It is also an advantage of the invention to provide an improved and consistent anastomosis result, without the reliance on the technique and skill of the physician.

SUMMARY OF THE INVENTION

These and other advantages of the invention are accomplished in accordance with the principles of the invention by providing an apparatus and methods for use in making an anastomotic connection between two tubular body fluid conduits in a patient, the connector being configured for attachment to the first and second tubular fluid conduits. In one embodiment of the invention, one of the tubular fluid conduits defines an opening extending between the exterior and the interior of the conduit. The connector may have an interior which is substantially accessible to the interior of the first tubular fluid conduit, and is also configured for annular enlargement. An expandable structure is provided having a first portion configured to annularly enlarge the connector by engaging the interior of the connector. In a preferred embodiment, a second portion of the expandable connector is configured to extend through the opening in the medial portion of the first tubular fluid conduit.

According to a preferred embodiment, a portion of the connector may be configured for attachment to the axial end of the first tubular fluid body conduit and be substantially coaxial therewith. The connector may include members having free end portions that are configured to penetrate the first tubular body conduit at locations that are axially spaced around the connector. An axial portion of the connector may be configured for insertion through an opening in a side wall of the second tubular fluid conduit. The connector may include members having free end portions that are directed radially outward and are configured to engage the exterior of the side wall of the second tubular fluid conduit when a predetermined axial portion of the connector has passed through the opening in the side wall of the second tubular fluid conduit.

In order to remotely expand the first, distal portion of the expandable structure, the expandable structure also includes a third, proximal portion for remotely introducing fluid or pressurized air. A tapered structure may be provided for dilating the opening in the second fluid tubular conduit by advancing the tapered structure through the opening. A longitudinal member may be provided which is configured to extend between the first tubular fluid conduit and the second tubular fluid conduit. In a preferred embodiment, the longitudinal member is configured to extend through the opening in the second tubular fluid conduit and along the lumen thereof. The tapered structure may also include an elongated tubular structure, e.g., a catheter-like structure, axially extending from an end portion of the tapered structure and coaxial with the longitudinal member. The tapered structure may be configured to be advanced into and along the interior of the second tubular fluid conduit after dilating the opening in the side wall thereof. Alternatively, the tapered structure is configured to be advanced into and along the interior of the first tubular fluid conduit after dilating the opening in the side wall of the second tubular body conduit. In such a case, the connector may have annularly expanded sufficiently to allow the tapered structure to pass through the interior of the connector. As an alternative or in addition to the tapered structure, a second expandable structure, such as a balloon, may be provided which is configured to dilate the opening in the second tubular fluid conduit.

Further in accordance with the invention, apparatus and methods are provided to make a second anastomotic connection between the first tubular fluid conduit and a third tubular fluid conduit. The first tubular fluid conduit defines first and second axial end portions. The apparatus further includes a second connector configured for attachment to the first and third tubular fluid conduits and having an interior thereof substantially accessible to the interior of the first tubular fluid conduit. The second connector is also configured for annular enlargement. A second expandable structure is provided having a first, distal portion configured to annularly enlarge the second connector by engaging the interior of the second connector, and having a portion configured to extend through the opening in the medial portion of the first tubular fluid conduit. The distal portion of the first expandable structure and the distal portion of the second expandable structure are independently and/or simultaneously expandable.

The first tubular fluid conduit may be a natural body conduit, such as the saphenous vein or the internal mammary artery, and the opening in a medial portion thereof may be a natural side branch. Alternatively, the first tubular fluid conduit may be an artificial graft conduit.

Further apparatus and methods for installing a tubular graft conduit between first and second spaced locations in a patient's tubular body structure are disclosed. Apparatus in accordance with the invention may include first and second connectors attached to the axial ends of the tubular graft conduit and having interior portions substantially accessible to the interior of the tubular graft conduit. A first expandable structure may be provided having a first balloon portion for annularly expanding a portion of the first connector by engaging the interior of the first connector and a first elongated structure for remotely expanding the first balloon member. The first expandable structure may be provided with an axial opening extending therethrough. A second expandable structure may also be provided having a second balloon portion for annularly expanding a portion of the second connector by engaging the interior of the second connector and a second elongated structure for remotely expanding the second balloon member. A portion of the second expandable structure may extend coaxially through the axial opening in the first expandable structure.

A method of installing the tubular graft conduit between first and second spaced locations in a patient's tubular body structure is disclosed, which includes providing an aperture through a wall of the tubular body structure at the first location with a distal portion of an elongated structure inserted into and along a lumen of the tubular body structure to the first location. A graft is provided having first and second connectors attached to axial ends of the graft.

The graft may be passed along the lumen of the tubular body structure through the wall at one of the first and second locations to the other of the locations. A further step may be to attach axial end portions of the graft to the tubular body structure adjacent the first and second locations by annularly expanding the first and second connectors. According to a preferred embodiment, the step of attaching axial end portions of the graft to the tubular body structure by annularly expanding the first and second connectors may be achieved by expanding first and second expandable structures positioned adjacent the interiors of the first and second connectors.

In accordance with a preferred embodiment, the step of attaching axial end portions of the graft to the tubular body structure may include annularly expanding a first axial portion of the first connector spaced furthest from the first location, inserting a second axial portion of the first connector into the tubular body structure at the first location such that the first axial portion of the first connector remains outside the tubular body structure, and annularly expanding the second axial portion of the first connector positioned inside the tubular body structure. In order to deploy the connector as described above, the method may include providing a second elongated structure having a lumen, coaxially positioned to surround an axial portion of the first connector. When the second elongated structure is provided in an embodiment in accordance with the invention, the first axial portion of the first connector may be exposed from the lumen of the second elongated structure while retaining the second axial portion within the lumen of the second elongated structure, before annularly expanding the first axial portion of the first connector. Moreover, before inserting a second axial portion of the first connector into the tubular body structure at the first location, the distal end portion of the first elongated structure may be retracted into the tubular body structure. In addition, before annularly expanding the second axial portion of the first connector positioned inside the tubular body structure at the first location, the second portion of the first connector may be exposed from the lumen of the second elongated structure.

Further features of the invention, its nature and various advantages will be more apparent from the accompanying drawings and the following detailed description of the preferred embodiments.

BRIEF DESCRIPTION OF THE DRAWINGS

FIG. 1(a) is a simplified sectional view, similar to FIG. 1, illustrating an alternative embodiment of the apparatus in accordance with the invention.

FIG. 12 is a simplified sectional view, showing the use of apparatus in an expanded configuration accordance with the invention.

FIG. 12(a) is an enlarged sectional view, showing the apparatus of FIG. 12 in an unexpanded configuration in accordance with the invention.

FIG. 13 is a simplified sectional view, showing an early stage in the use of the FIG. 1 apparatus and the FIG. 2 connector in accordance with the invention.

FIG. 13(a) is a simplified sectional view, similar to FIG. 13, showing an alternative embodiment of the use of the FIG. 1 apparatus and the FIG. 2 connector in accordance with the invention.

FIG. 21 is a simplified sectional view showing an early stage in the method in accordance with the invention.

FIG. 22 is a simplified sectional view similar to FIG. 21, showing a later stage in the method in accordance with the invention.

FIG. 23 is a simplified sectional view similar to FIG. 21, showing a still later stage in the method in accordance with the invention.

FIG. 24 is a simplified sectional view similar to FIG. 21, showing yet a later stage in the method in accordance with the invention.

FIG. 27 is a simplified sectional view showing a portion of the FIG. 25 view, showing a still later stage in the use of the FIG. 20 apparatus in accordance with the invention.

FIG. 28 is a simplified sectional view similar to FIG. 27, showing the end result of using the FIG. 20 apparatus and the FIG. 5 connector in accordance with the invention.

DETAILED DESCRIPTION OF THE PREFERRED EMBODIMENTS

Although the invention has other possible uses, the invention will be fully understood from the following explanation of its use in providing a bypass around a narrowing in a patient's vascular system. In addition to providing a coronary artery bypass, the invention is useful anywhere in the patient's circulatory system including renal veins and arteries, femoral veins and arteries, abdominal aorta, peripheral bypass in the arms and legs of the patient, A-V shunts, carotid artery, and any other circulatory system bypass. The bypass graft may be a vein, radial artery, internal mammary artery (IMA), other native vessel, or synthetic conduit.

Figure 1:
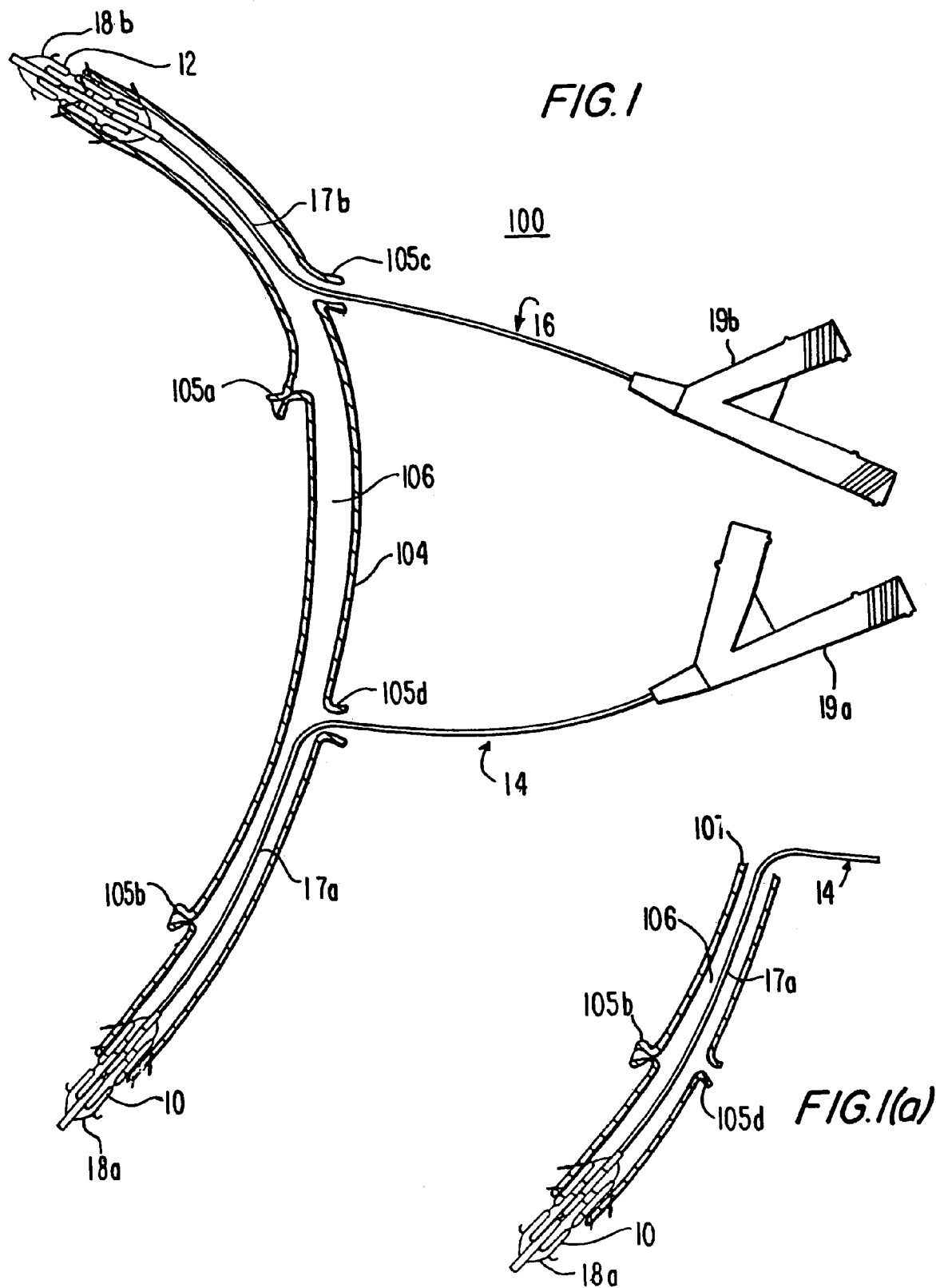
FIG. 1 is a simplified view, in partial section, of the apparatus in accordance with the invention.

FIG. 1 illustrates apparatus 100 for installing a graft 104 to the patient's vascular system. Apparatus 100 includes a connector structure 10 useful for making the connection between the graft 104 and the coronary artery (not shown in the FIG.), typically referred to as the "distal" connection. Connector structure 12 is particularly useful for making the connection between the graft 104 and the arterial blood source, such as the aorta (not shown in the FIG.). The invention is also useful when the arterial blood source is the internal mammary artery (IMA) and a single connection is made, i.e., connector 10 is used to connect a severed portion of the IMA to the coronary artery.

Connector structures 10 and 12 are deployed and installed by graft installing apparatus 14 and 16, respectively. As will be described in greater detail below, graft installing apparatus 14 and 16 actuate connector structures 10 and 12 by the expansion of connector expanding balloons 18a and 18b, via the introduction of fluid from proximal portions 19a and 19b to balloon catheters 17a and 17b, respectively. In a preferred embodiment of the invention, graft 104 may be a natural vessel that has been excised or relocated within the patient, such as the saphenous vein or IMA. The saphenous vein, for example, has a plurality of openings, such as side branches 105, that normally allow fluid flow between surrounding tissue and the vein itself. Many of these side branches, i.e., branches 105a and 105b, are typically sealed by tying off or stapling. However, at least one of the side branches, i.e., branches 105c and 105d, remain in fluid communication with the main lumen 106 of the graft 104. The open side branches 105c and 105d permit access to the interior lumen 106 of graft 104 and the interior of connectors structures 10 and 12. Use of the open side branches to introduce instrumentation into the interior lumen of graft conduit 104 for the purposes described above may reduce the trauma to the graft segment by obviating the need for a venotomy or other incision in the graft. When synthetic graft materials are used, the graft may be manufactured with side branches or openings to permit access to the interior of the graft in a substantially similar manner. Connectors 10 and 12 may be deployed individually or simultaneously, as operative conditions may suggest or the physician's evaluation may deem advantageous. Connectors 10 and 12 are expanded simultaneously by simultaneous expansion of balloons 18a and 18b. Individual expansion of connectors 10 and 12 is achieved by individual expansion of single ones of balloons 18a and 18b.

FIG. 1 illustrates graft installing apparatus 14 and graft installing apparatus 16 passing through open side branches 105d and 105c, respectively. It is understood that graft installing apparatus 14 may access the interior 106 of graft 104 and the interior of connector 10 through an axial end portion 107 of graft 104, as illustrated in FIG. 1(a). The approach of accessing the connector 10 through an axial end portion 107 of the graft 104 may be advantageous when an anastomosis is performed at a first end portion of the graft 104, and subsequently at a second end portion. During such a procedure, the first connector may be accessed through an axial end portion of graft 104, as shown in FIG. 1(a). The second connector may then be accessed through a side branch, such as side branch 105c, as shown in FIG. 1.

Figure 2:
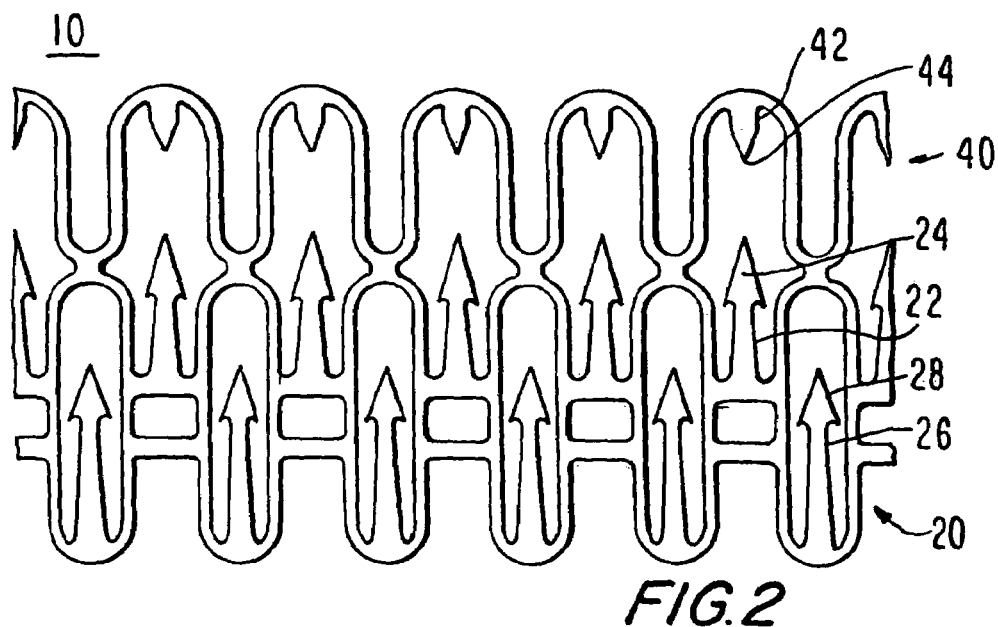
FIG. 2 is a simplified planar development of the structure of an illustrative embodiment of a connector constructed in accordance with this invention.
Figure 3:
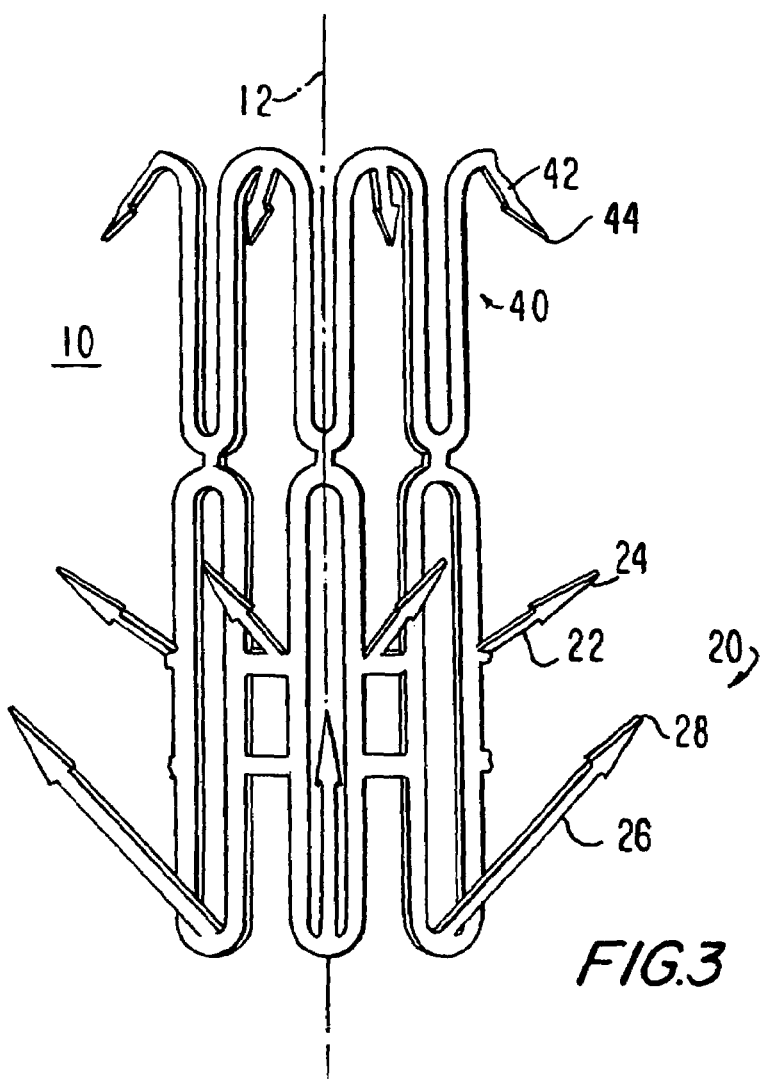
FIG. 3 is a simplified elevational view of the actual structure of the connector which is shown in planar development in FIG. 2.

FIG. 2 shows a planar development of what is actually an integral, one-piece (unitary), annular connector structure 10. Structure 10 is substantially identical to the connector described in Swanson et al. U.S. Pat. No. 6,113,612, which is incorporated by reference in its entirety herein, and the differences are noted herein. In particular, the left and right edges of the structure shown in FIG. 2 are actually joined to and integral with one another. Thus the actual structure is as shown in FIG. 3, although FIG. 2 is useful to more clearly reveal the details of various features of the structure. A central longitudinal axis 12 about which structure 10 is annular is shown in FIG. 3.

An illustrative material for structure 10 is 304 stainless steel. Other examples of suitable materials include tantalum, tungsten, platinum, and nitinol. Structure 10 may be advantageously produced by starting with a single, unitary metal tube and removing selected material until only the structure shown in FIG. 3 remains. For example, laser cutting may be used to remove material from the starting tube in order to produce structure 10. Although connector 10 can be made in various sizes for various uses, a typical connector has an initial outside diameter in the range from about 0.040 to about 0.065 inches, an initial length of about 4.0 mm, and a material thickness of about 0.004 inches.

Connector 10 may be described as including axially spaced first and second portions 20 and 40, respectively. First portion 20 includes a first plurality of annularly spaced members 22 that in this case have free end portions 24 that are sharply pointed and that point towards second portion 40. In addition, first portion 20 also includes a second plurality of annularly spaced members 26, preferably having free end portions 28 that are sharply pointed and point towards second portion 40. Each of members 22 and 26 is deflectable radially out from the remainder of structure 10 as shown, for example, in FIG. 3. This outward deflection is preferably at least partly plastic.

Second portion 40 also includes a plurality of annularly spaced members 42 that in this case have free end portions 44 that are sharply pointed and that point toward first portion 20. Each of members 42 is deflectable radially out from the remainder of structure 10 as shown, for example, in FIG. 3. Again, this outward deflection is preferably at least partly plastic.

The above-mentioned outward deflection of elements 22, 26 and 42 can be produced by putting the connector on a mandrel and prying elements 22, 26 and 42 radially outward. Elements 22, 26 and 42 act as retention means for securing the connector 10 to the graft 104 as described below. It is understood that when artificial (synthetic) grafts are used, different retention means, such as suture loops, may be used.

Figure 4:
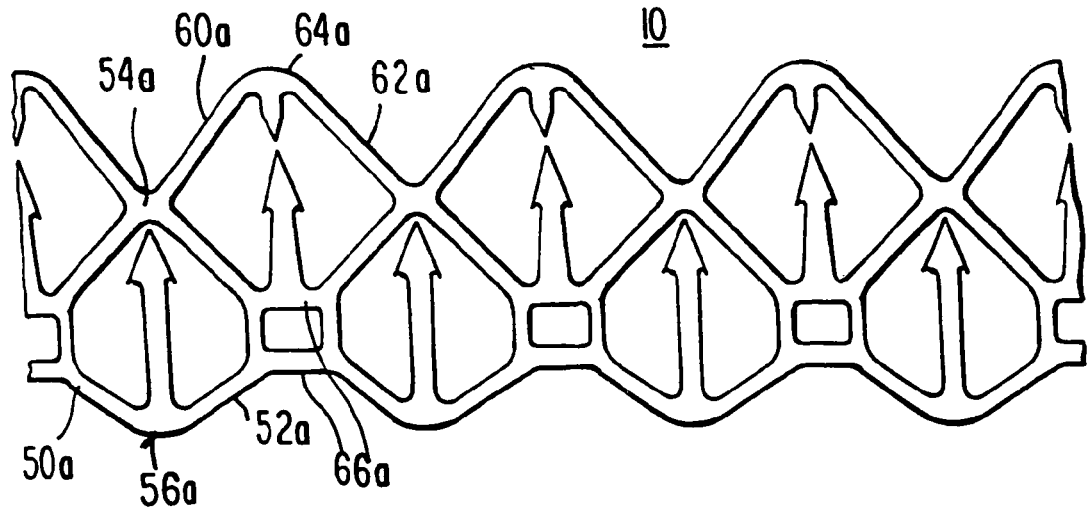
FIG. 4 is a simplified planar development of the structure of FIGS. 2-3 showing that structure's capacity for annular enlargement in accordance with the invention.

Connector 10 is formed in such a way that it is annularly enlargeable (e.g., by inflation of a balloon that is temporarily disposed inside the connector). The annularly expanded condition of connector 10 is shown in FIG. 4. The annular expansion of connector structure 10 is described in greater detail in U.S. Pat. No. 6,113,612, incorporated by reference above. The annular expandability of connector 10 is provided by making the connector with a plurality of annularly adjacent, annularly enlargeable cells. For example, a typical cell includes annularly spaced, but adjacent, longitudinal members 50a and 52a, the axially spaced ends of which are connected to one another at 54a and 56a. A plurality of these cells are connected side to side on connector structure 10. A representative one of another cell includes annularly adjacent longitudinal members 60a and 62a, the axially spaced ends of which are connected at 64a and 66a. These cells are connected side to side at portion 40 of connector structure 10. The structure is annularly enlargeable by annularly enlarging these cells as shown, for example in FIG. 4. It will be appreciated that as structure 10 annularly enlarges, it generally axially shortens.

Figure 7:
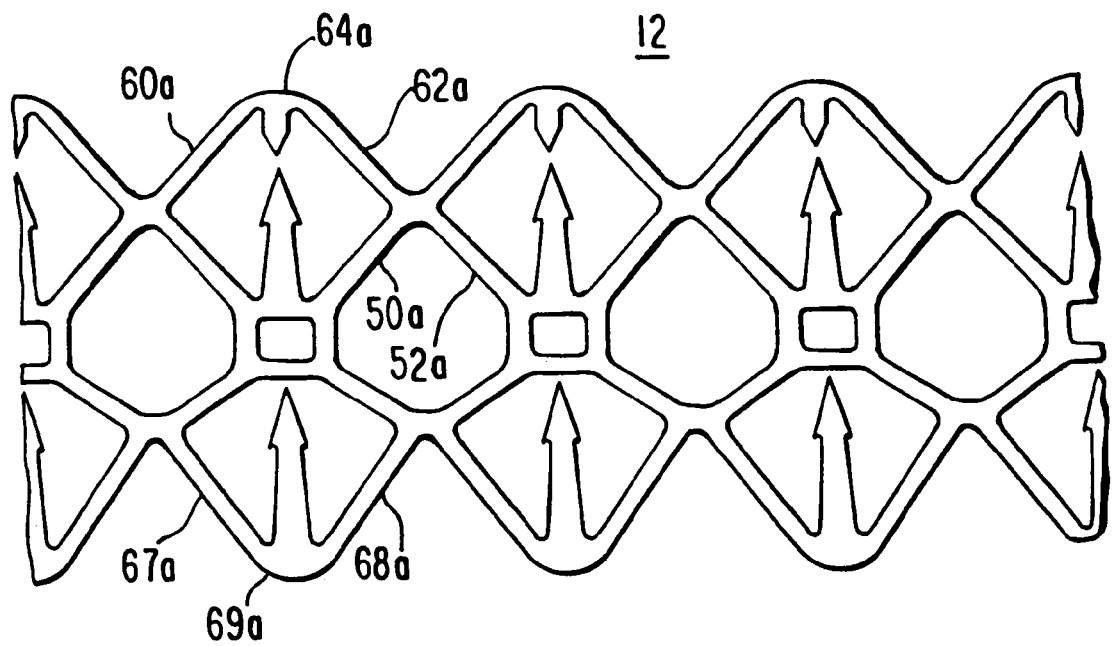
FIG. 7 is a simplified planar development of the structure of FIGS. 5-6 showing that structure's capacity for annular enlargement in accordance with the invention.
Figure 5:
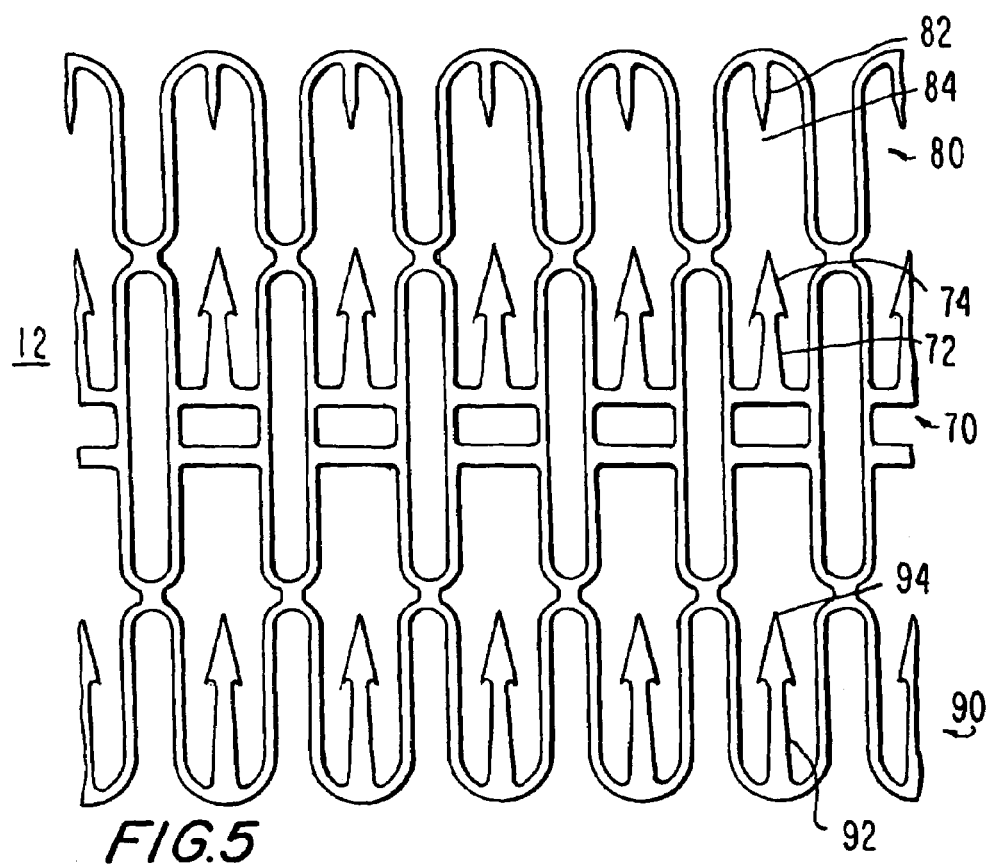
FIG. 5 is a simplified planar development of the structure of a second illustrative embodiment of a connector constructed in accordance with this invention.
Figure 6:
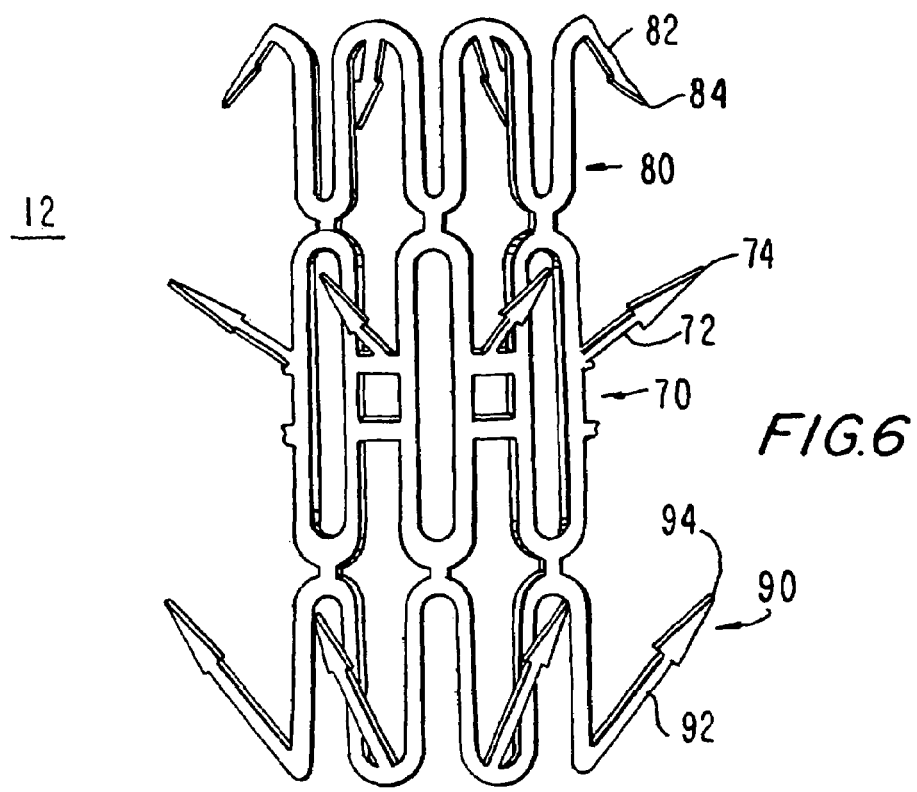
FIG. 6 is a simplified elevational view of the actual structure of the connector which is shown in planar development in FIG. 5.

FIGS. 5-7 illustrate an alternative embodiment of a connector structure, i.e., connector structure 12, which is substantially similar to connection structure 10 described above, and the connector described in U.S. Pat. No. 6,113,612, incorporated by reference above. Connector 12 is advantageously useful in making the proximal anastomosis between the graft and the aorta. Many of the differences between connector structure 12 and connector structure 10, described above, are relevant to the different characteristics of the aortic wall, which is thicker and more rigid than the coronary artery wall. The particular sizes and configurations of the connector structures described herein may be specifically tailored to the type of conduit being anastomosed. For example, in the exemplary procedure, the aorta wall is greater than 2 mm thick and the coronary artery wall is usually less than 1 mm thick. Therefore, connector 10 and 12 are constructed to secure the graft to the respective vessel walls.

Connector 12 may be described as including axially spaced first portion 70, substantially identical to first portion 20 of connector 10, second portion 80, substantially identical to second portion 40, and third portion 90. First portion 70 includes a first plurality of annularly spaced members 72 that in this case have free end portions 74 that are sharply pointed and that point towards second portion 80. Second portion 80 includes a plurality of annularly spaced members 82 that are sharply pointed and point towards first portion 70. In addition, third portion 90 includes a plurality of annularly spaced members 92, preferably having free end portions 94 that are sharply pointed and point towards second portion 70, and in substantially the same direction as members 72. Each of members 72, 82 and 92 is deflectable radially out from the remainder of structure 12 as shown, for example, in FIG. 6. This outward deflection is preferably at least partly plastic.

Connector 12 is annularly enlargeable as described above for connector 10. The annularly expanded condition of connector 12 is shown in FIG. 7. As described for connector 10, connector 12 is provided with annularly adjacent, annularly enlargeable cells. Connector 12 also defines a series of enlargeable cells defined by adjacent longitudinal members 67a and 68a, the axially spaced ends of which are connected at 66a and 69a.

Figure 8:
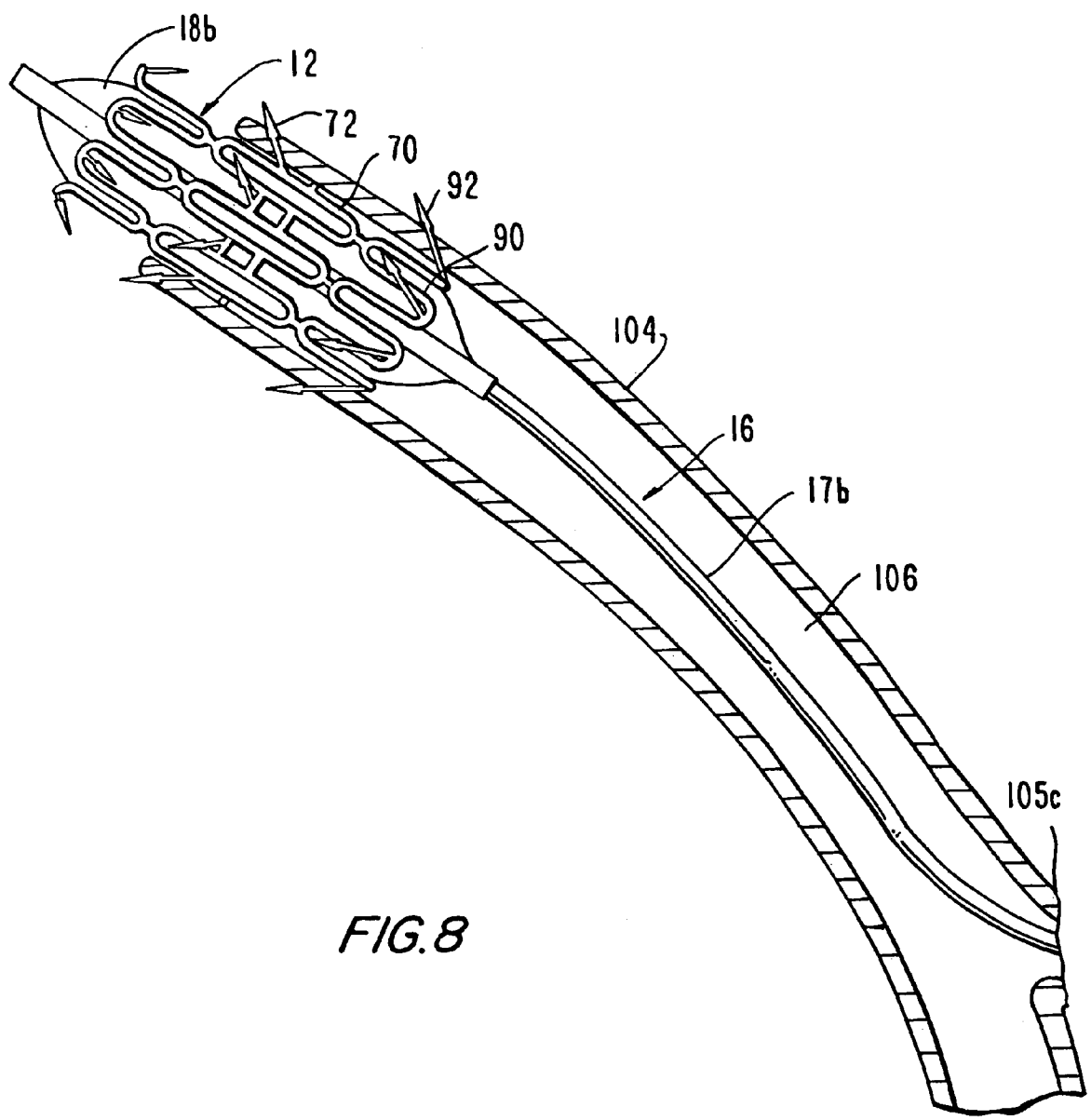
FIG. 8 is simplified view in partial section of the structure of FIG. 7 with additional illustrative apparatus shown in FIG. 1 for use in delivering and deploying the FIG. 6 structure in a patient in accordance with the invention.

FIG. 8 illustrates exemplary connector 12 positioned with respect to graft installing apparatus 16. In particular, balloon 18b in its uninflated configuration is positioned within the interior of connector 12. The remainder of the graft installing apparatus (e.g., balloon catheter 17b) extends within lumen 106 and through side branch 105c.

Graft 104 is positioned annularly around the first portion 70 and third portion 90 of connector 12. Graft 104 may be a natural body conduit, such as the saphenous vein or IMA, or an artificial graft conduit, or a combination of natural and artificial conduits. Graft conduit 104 is placed on connector 12 such that radially outwardly deflected members 72 and 92 penetrate and pass through the side wall of graft 104. The graft attachment is described in greater detail in U.S. Pat. No. 6,113,612, incorporated by reference above. By positioning the graft conduit 104 around connector 12, the interior of connector 12 is accessible, in communication with, or open to the interior lumen of graft conduit 104. It is understood that a portion of the connector 12 may be alternatively positioned outside the graft conduit 104; however, a portion of the connector 12 should remain accessible from the interior of the graft 104.

Figure 9:
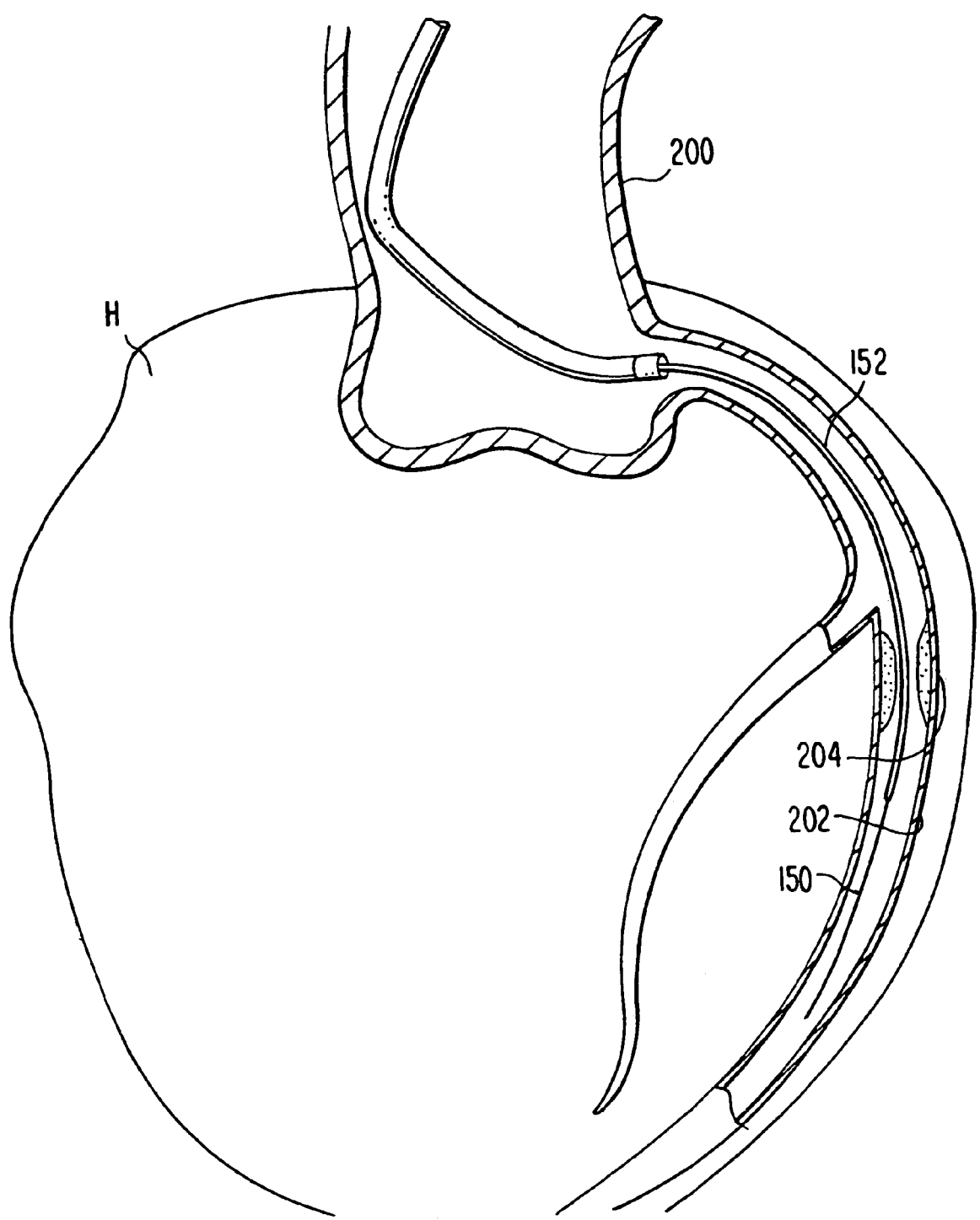
FIG. 9 is a simplified sectional view showing an early stage in the method in accordance with the invention.

Graft conduit 104 may be installed in the patient and attached by connectors 10 and 12 by methods described herein. The example illustrates the process of connecting graft 104 to the aorta 200 and the coronary artery 202 downstream of the narrowing 204 of the patient's heart H. According to a first method, illustrated in FIGS. 9-11, a guide member is installed from inside the coronary artery 202 to the outside, and assists in the installation of the graft 104 and the connector 10. The installation of the guide member is described in greater detail in Goldsteen et al. U.S. Pat. No. 5,976,178 and published Patent Cooperation Treaty ("PCT") patent publication No. WO 00/27312, published May 18, 2000, both of which are incorporated by reference in their entirety herein. As FIG. 9 illustrates, a first guide wire 150 is introduced in the patient's circulatory system via a remote location, such as the femoral artery (not shown). Guide wire 150 is advanced from the aorta 200 into the coronary artery 202 having a narrowing 204. Guide wire is preferably advanced through the narrowing 204.

With continued reference to FIG. 9, a catheter or catheter-like structure 152 is introduced into the patient over and along guide wire 150, once wire 150 is positioned across narrowing 204. Guide wire 150 facilitates passage of the distal portion of catheter 152 through narrowing 204. As shown in FIG. 9, catheter 152 substantially follows the contours of wire 150.

Figure 10:
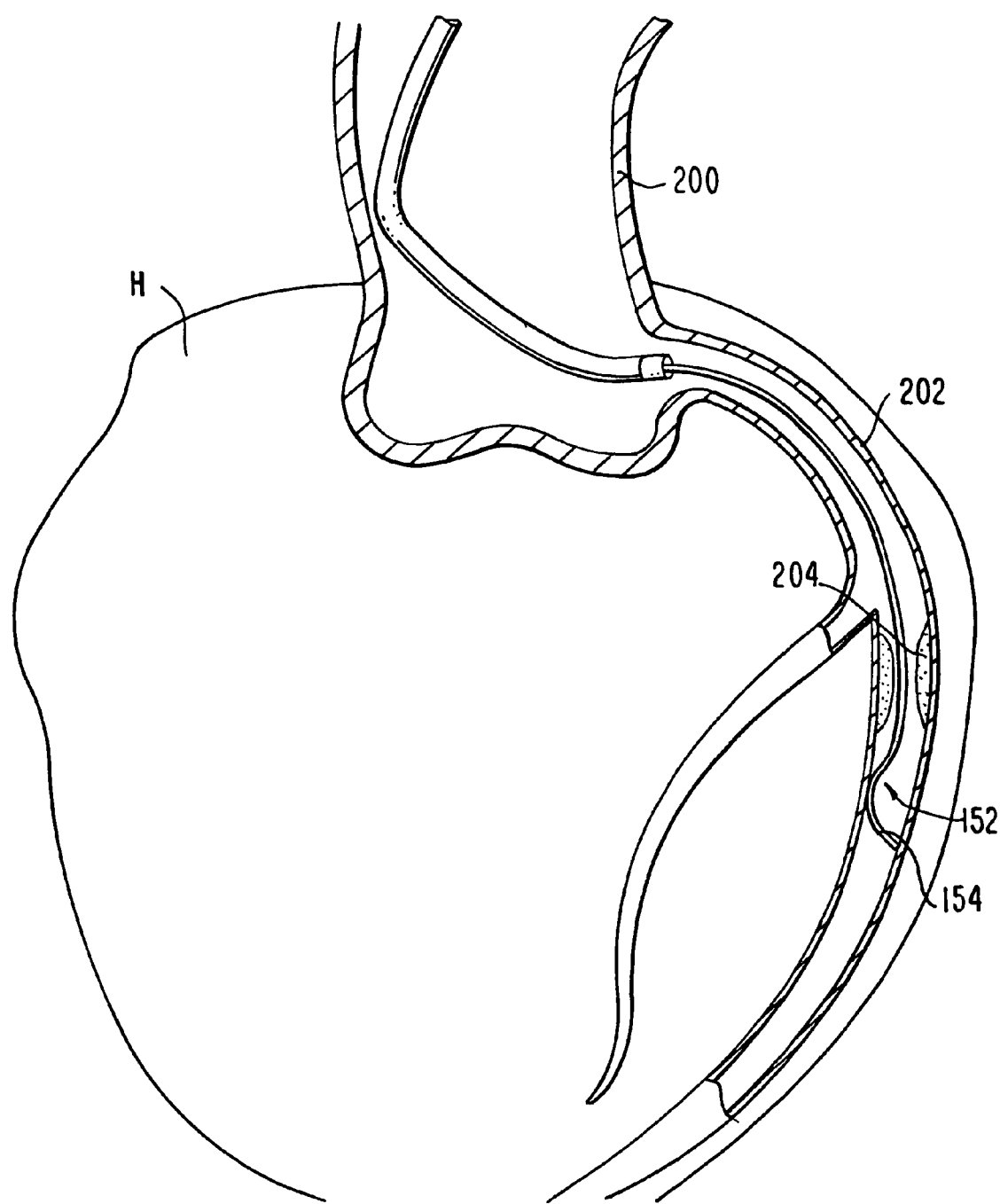
FIG. 10 is a simplified sectional view similar to FIG. 9, showing a later stage in the method in accordance with the invention.

An end portion 154 of catheter 152 is preferably constructed to form a laterally extending arch as shown in FIG. 10 when guide wire 150 is withdrawn from catheter 152. For example, catheter 152 may be made so that it resiliently tends to form an arch of a predetermined lateral extent when it is freed from the straightening effect of guide wire 150. An internal lumen (not shown) preferably extends along the entire length of the catheter and is used to allow the catheter 152 to track over guide wire 150 as described above, and to subsequently guide a longitudinal piercing structure to the point on the wall of artery 202 where it is desired to connect one end of a bypass graft.

As shown in FIG. 10, a distal portion 154 of the catheter 152 may be configured to deflect or curve to the side when guide wire 150 is withdrawn as described in PCT publication No. WO 00/27312, or alternatively the distal end of the lumen within the catheter may be shaped to deflect the guide wire laterally, as described in U.S. Pat. No. 5,976,178, both of which are incorporated by reference above. As yet another alternative, the lumen in catheter 152 may have a side branch which exits from the side wall of the catheter at or near the apex of an arch in the catheter adjacent the coronary artery wall, as described in PCT publication No. WO 00/27312, incorporated by reference above.

Figure 11:
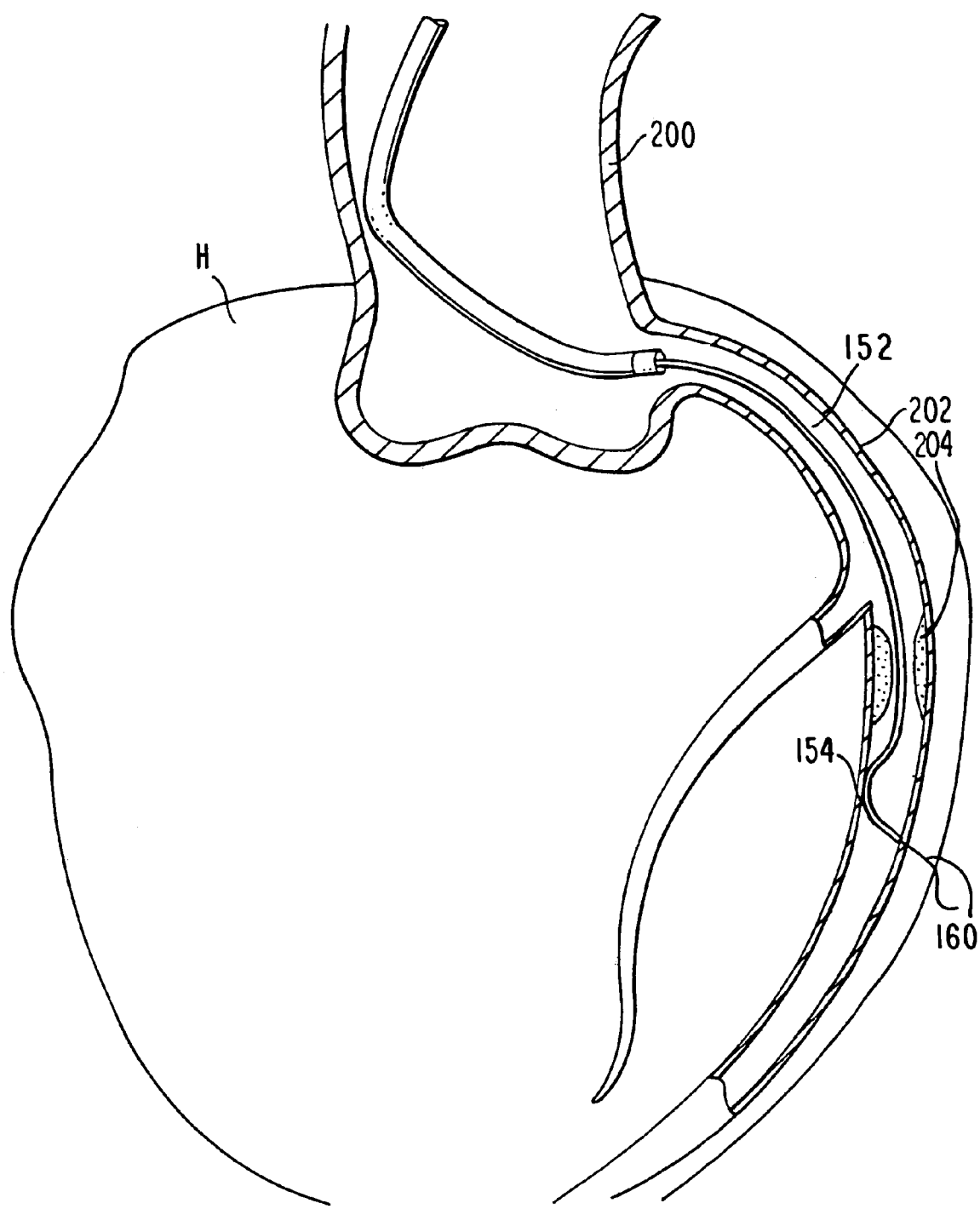
FIG. 11 is a simplified sectional view similar to FIG. 10, showing a still later stage in the method in accordance with the invention.

As illustrated in FIG. 11, a subsequent step involves inserting an elongated piercing structure, or guide member 160 (e.g., primarily a metal wire or wire-like structure), into catheter 152 along the lumen thereof formerly used for guide wire 150. Because catheter portion 154 is now arched as shown in FIGS. 10-11, the distal end of guide member 160 tends to follow the lumen of catheter 152 and into contact with the interior surface of the side wall of coronary artery 202. The distal tip of guide member 160 is sufficiently sharp and guide member 160 is sufficiently stiff that the distal tip of guide member 160 can be pushed out through the coronary artery wall tissue.

FIGS. 12-12(a) illustrate a preferred embodiment in which an expandable member may be used in a further step of the procedure. An expandable member, such as aperture dilating balloon 170, may be provided on the distal end of catheter 172. Catheter 172 is advanced over and along guide member 160, through the vascular system, to the anastomotic site. In the example, balloon 170 is advanced through the aorta 200, into the coronary artery and through the narrowing 204. As shown in FIG. 12(a), balloon 170 is inserted through the aperture in the coronary artery wall made by guide member 160. Balloon 170 passes through the aperture in its unexpanded state. The balloon 170 is subsequently expanded by the introduction of fluid or air into catheter 172, as shown in FIG. 12, in order to controllably dilate the aperture in the wall of the coronary artery 202 to a size which may be suitable for the requirements of the distal connector or other apparatus useful to make the anastomosis.

FIG. 13 illustrates additional apparatus which may be used in a further step of the procedure. A gradually tapered nose portion or sheath, such as nose portion 180, may be provided having a substantially conical outer surface. Nose portion 180 surrounds the distal portion of balloon 18a and connector 10. More particularly, nose portion covers outwardly extending members 42 with free ends 44. This geometry allows optimal passage across a body conduit wall (e.g., a coronary artery wall as shown in FIG. 13 and described below) with minimal wall damage, with minimal force being required, and with no catching or snagging on the wall. An inside portion of nose portion 180 may be shaped to receive balloon 18a, connector 10, and a distal portion of graft 104.

According to a first embodiment, portion 180 is attached to a catheter 182 adjacent the narrow distal end of portion 180 and extends distally from portion 180. Catheter 182 may be introduced over guide wire 160 from a surgical access opening. Catheter 182 would subsequently be advanced over guide wire 160 until it exits the patient at the remote location where the guide wire 160 exits the patient, e.g., the leg adjacent the femoral artery. This configuration, illustrated in FIG. 13, allows the nose portion 180 to be pulled upstream within the coronary artery 202, as will be described in greater detail below. According to an alternative embodiment, portion 180' may be connected to a catheter portion 182' which extends proximally from portion 180' and into graft 104 and graft installing apparatus 14 (FIG. 13(a)). This configuration preferably enables portion 180' to be withdrawn proximally into graft 104 after completion of the anastomosis.

With continued reference to FIG. 13, a typical use of apparatus 14 and nose portion 180 as shown is to deliver graft 104 for connection to an aperture in a side wall of a patient's tubular body conduit, e.g., a coronary artery 202 requiring a bypass graft. A surgical access opening is made in the patient adjacent the anastomotic site in order to insert the distal end portion of graft installing apparatus 14 (e.g., balloon 18a), graft 104 and connector 10 into the patient. Apparatus 14 is positioned such that a portion of apparatus 14 passes through a side branch 105d of graft 14 to access an interior portion of connector 10.

Guide member 160 may be inserted into an axial lumen at the distal portion of balloon 18a. The tapered nose portion 180 is then gradually forced into the aperture as illustrated by the arrow (e.g., by using balloon 18a to push portion 180 distally into the aperture) to dilate the aperture. The natural elastic recoil of the conduit 202 side wall tissue may continue to keep the aperture sealed or substantially sealed around portion 180.

Figure 14:
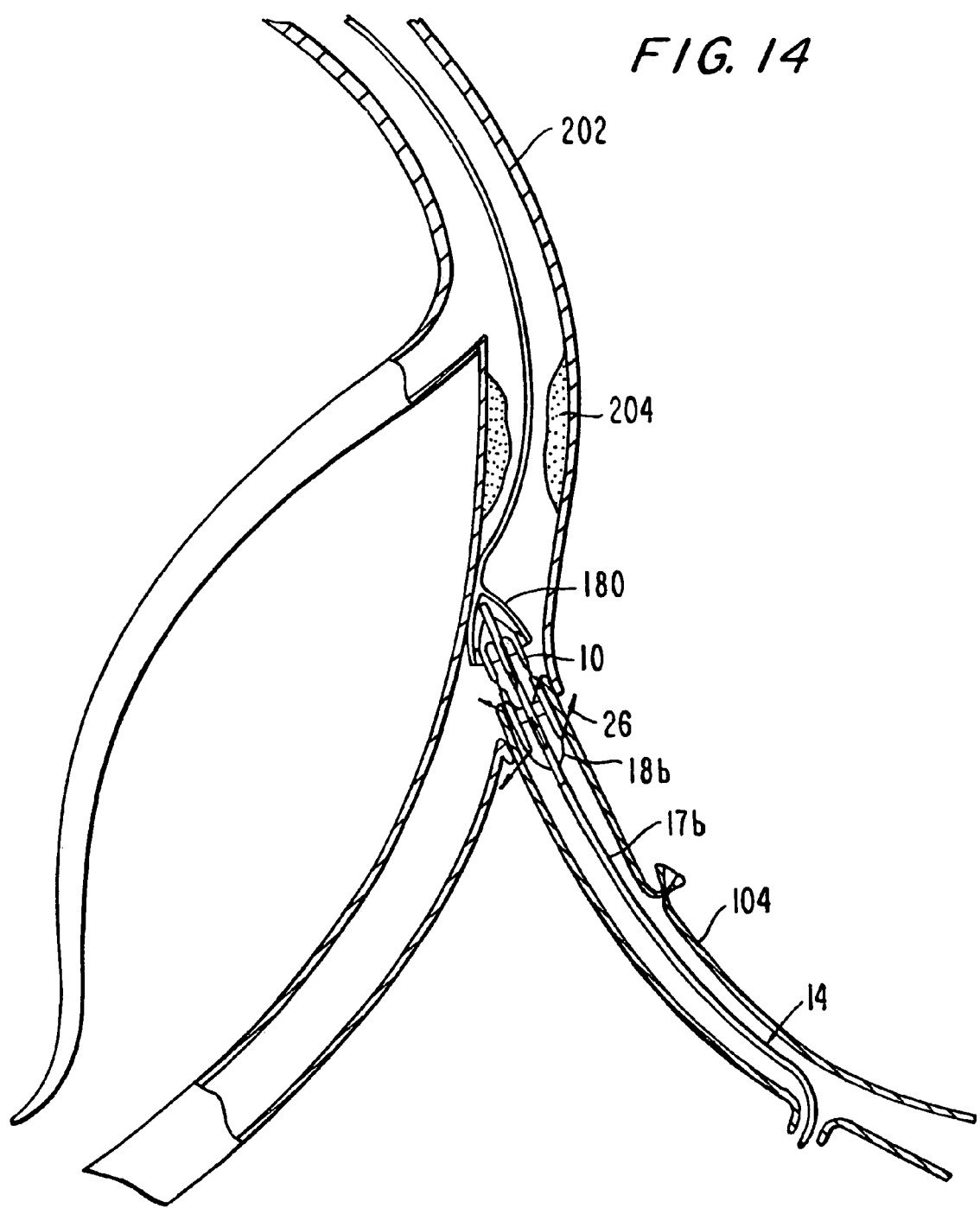
FIG. 14 is a simplified sectional view similar to FIG. 13, showing a later stage in the use of the FIG. 1 apparatus in accordance with the invention.

As illustrated in FIG. 14, nose portion 180 is pushed far enough into the aperture in the side wall of conduit 202 so that connector 10 is part way through the aperture. The second plurality of members 26 of connector 10 are directed radially outward and engage the wall of conduit 202 after connector 10 has passed a predetermined distance into the aperture. Thus members 26 act as "stops" to assist in the positioning of connector 10 with respect to conduit 202.

Figure 15:
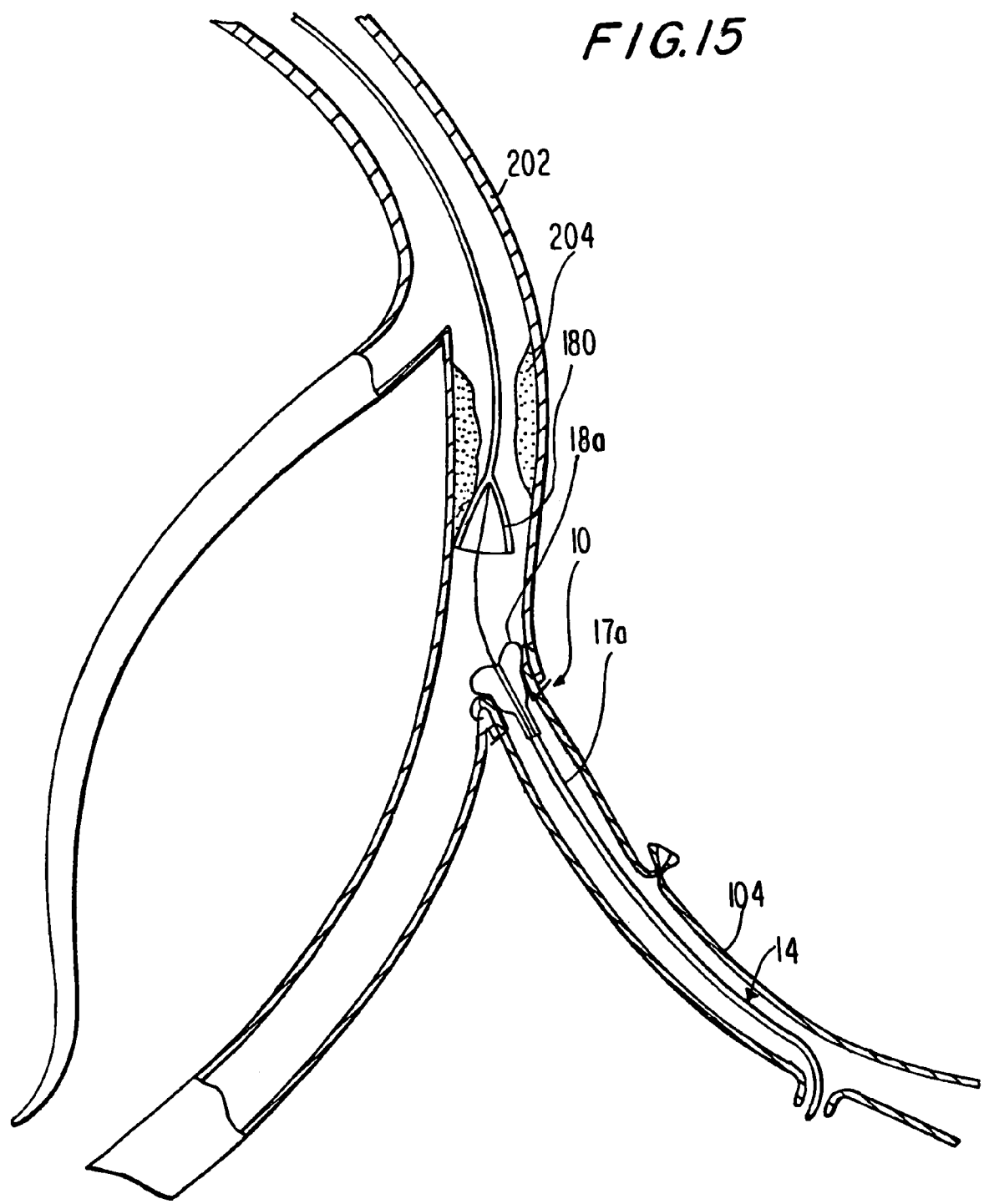
FIG. 15 is a simplified sectional view similar to FIG. 13, showing a still later stage in the use of the FIG. 1 apparatus in accordance with the invention.

FIG. 15 illustrates that the next step is to push nose portion 180 farther into conduit 202 (e.g., by pulling catheter 182 further upstream). This causes distal nose portion 180 to separate from connector 10, thereby exposing the connector and leaving it in the aperture through the conduit 202 side wall.

With continued reference to FIG. 15, the next step in use of apparatus 14 is to inflate balloon 18a. The balloon is typically sized to a specific anastomosis size (e.g., 3 millimeters diameter, 4 millimeters diameter, etc.). Inflation of the balloon forces connector 10 to annularly enlarge by enlarging cells 50/52/54/56 and 60/62/64/66 in the annular direction (See, FIG. 4). In addition, the portions of members 60 and 62 that are adjacent to elements 64 (as well as elements 64 and 42) are deflected radially out beyond other portions of the connector inside the side wall of conduit 202, thereby causing the extreme distal end of graft 104 to similarly flare out inside that side wall. This outward flaring of portions of connector 10 and graft 104 helps secure the connector and graft to the side wall of conduit 202, and also helps seal the graft to the conduit. The axial shortening of connector 10 that accompanies annular enlargement ensures that graft 104 is drawn into secure and fluid-tight engagement with conduit 202. The free ends of members 42 preferably penetrate the side wall of conduit 202 to further secure connector 10 and graft 104 in the aperture in the side wall. Members 50, 52, 56, and 24 may also flare out somewhat outside the side wall of graft 202 to help ensure that graft 104 remains open where it connects to conduit 202. Further details with regard to the installation of connector 10 are described in U.S. Pat. No. 6,113,612, incorporated by reference above.

Figure 16:
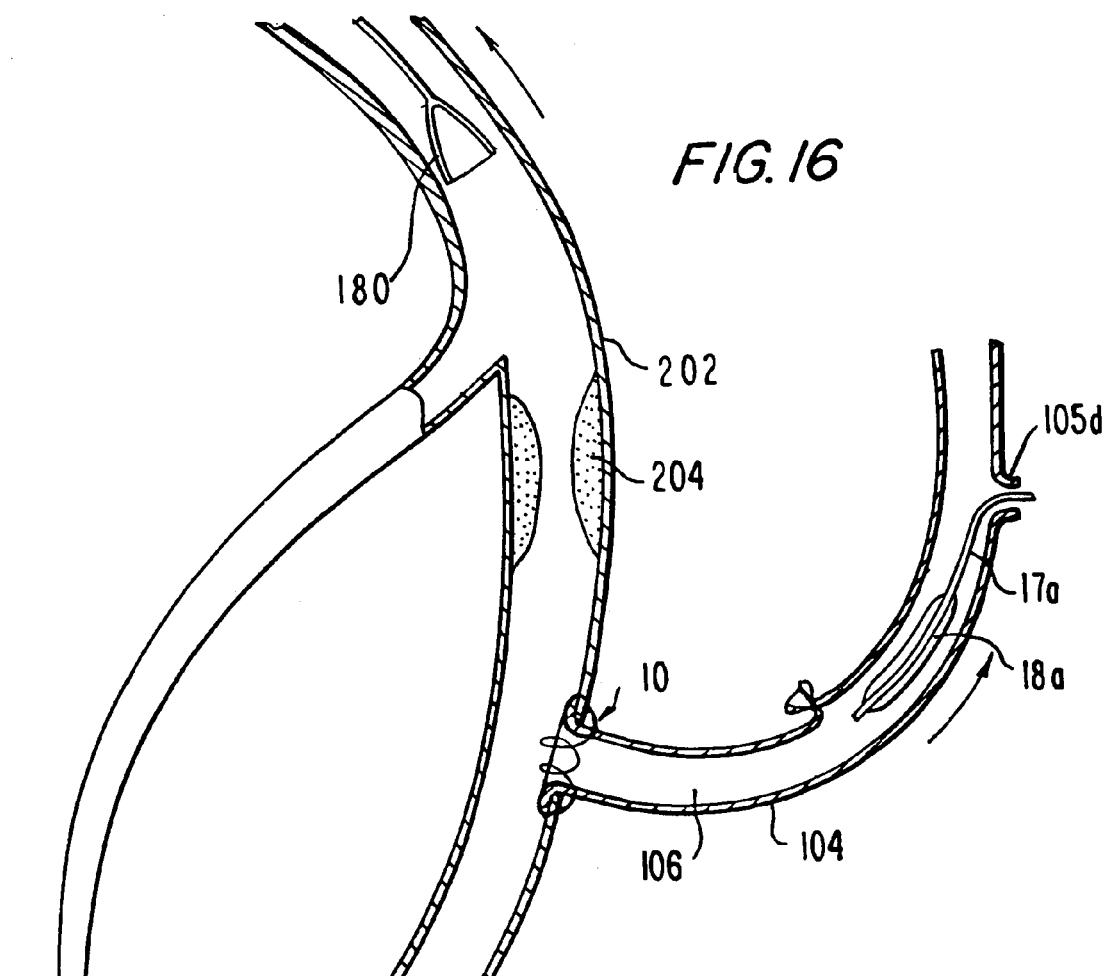
FIG. 16 is a simplified sectional view similar to FIG. 13, showing the end result of using the FIG. 1 apparatus and the FIG. 2 connector in accordance with the invention.
Figure 16A:
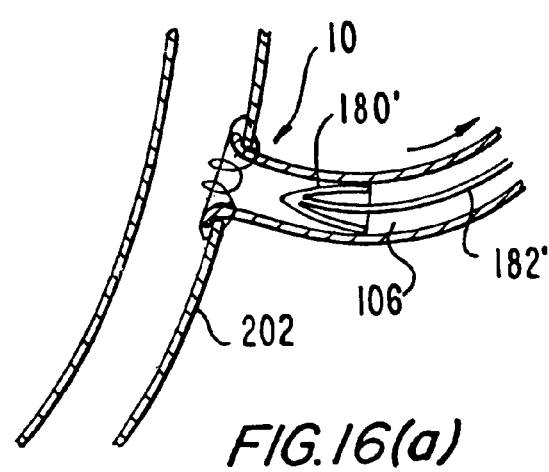
FIG. 16(a) is a simplified sectional view similar to FIG. 16, showing the alternative embodiment of FIG. 13(a) in accordance with the invention.

The next step in use of apparatus 14 is to deflate balloon 18a and withdraw all of elements 14, 17a, and 18a (e.g., by pulling them proximally out of graft 104). The nose portion 180 may be withdrawn as well (e.g., pulling portion 180 upstream by catheter 182, as indicated by the arrow. Alternatively, portion 180' is pulled proximally out of graft 104 if connector 10 is sufficiently enlarged to allow portion 180' to pass within connecter 10, as illustrated in FIG. 16(a)). This leaves the axial end portion of graft 104 connected to the side wall of conduit 202 by annularly enlarged connector 10 as shown in FIG. 16. In particular, in this example connector 10 provides an end-to-side anastomosis between graft 104 and conduit 202. Body fluid from graft 104 is able to flow into conduit 202 via this connection. Connector 10 presses graft 104 radially outward against the aperture through the side wall of conduit 202 all the way around that aperture, thereby preventing body fluid from leaking out of conduits 120 and 202. Connector 10 also prevents the end of conduit 120 from pulling out of the side wall of conduit 202.

Figure 17:
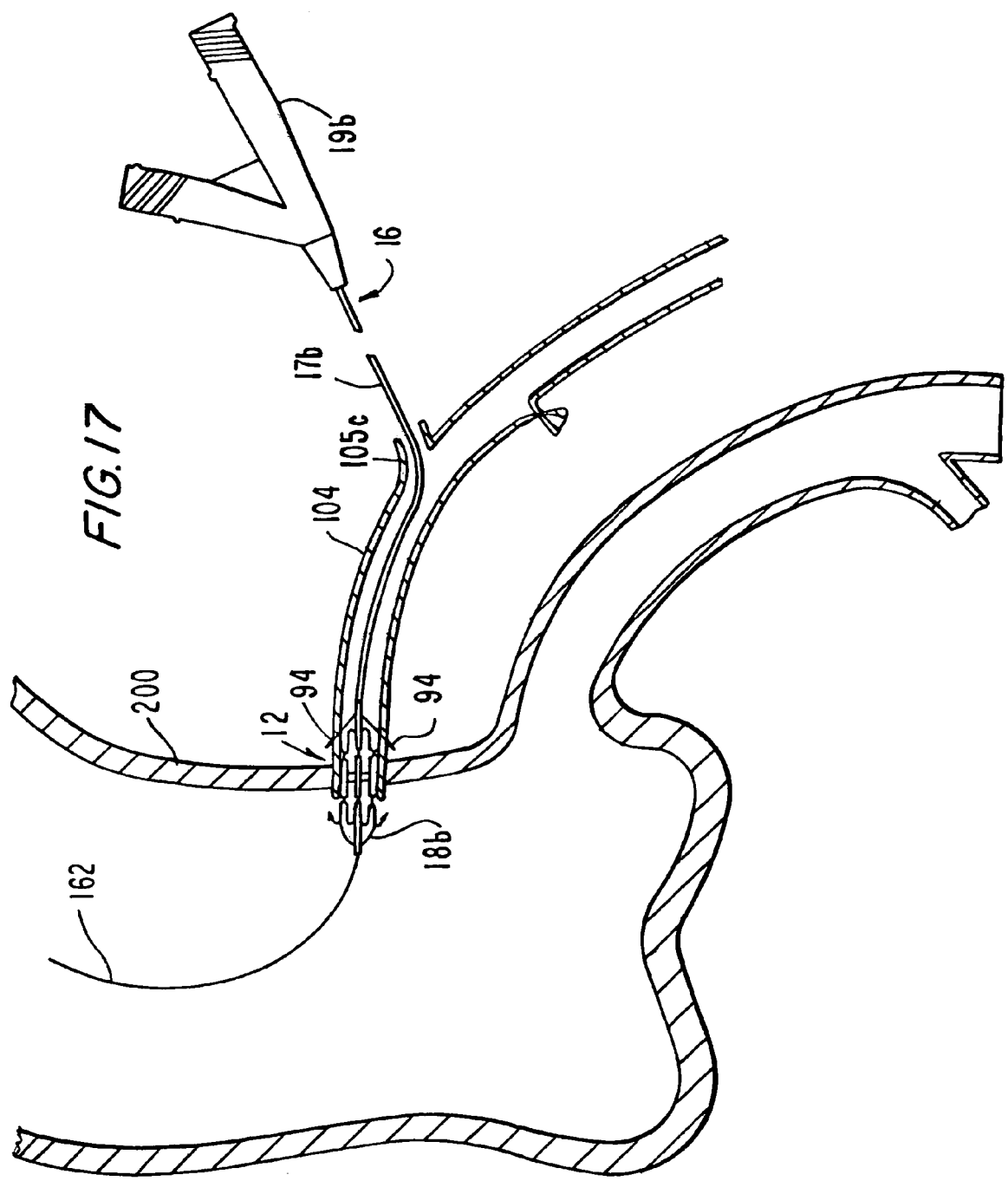
FIG. 17 is a simplified enlarged sectional view, showing an early stage in the use of the FIG. 1 apparatus and the FIG. 5 connector in accordance with the invention.
Figure 18:
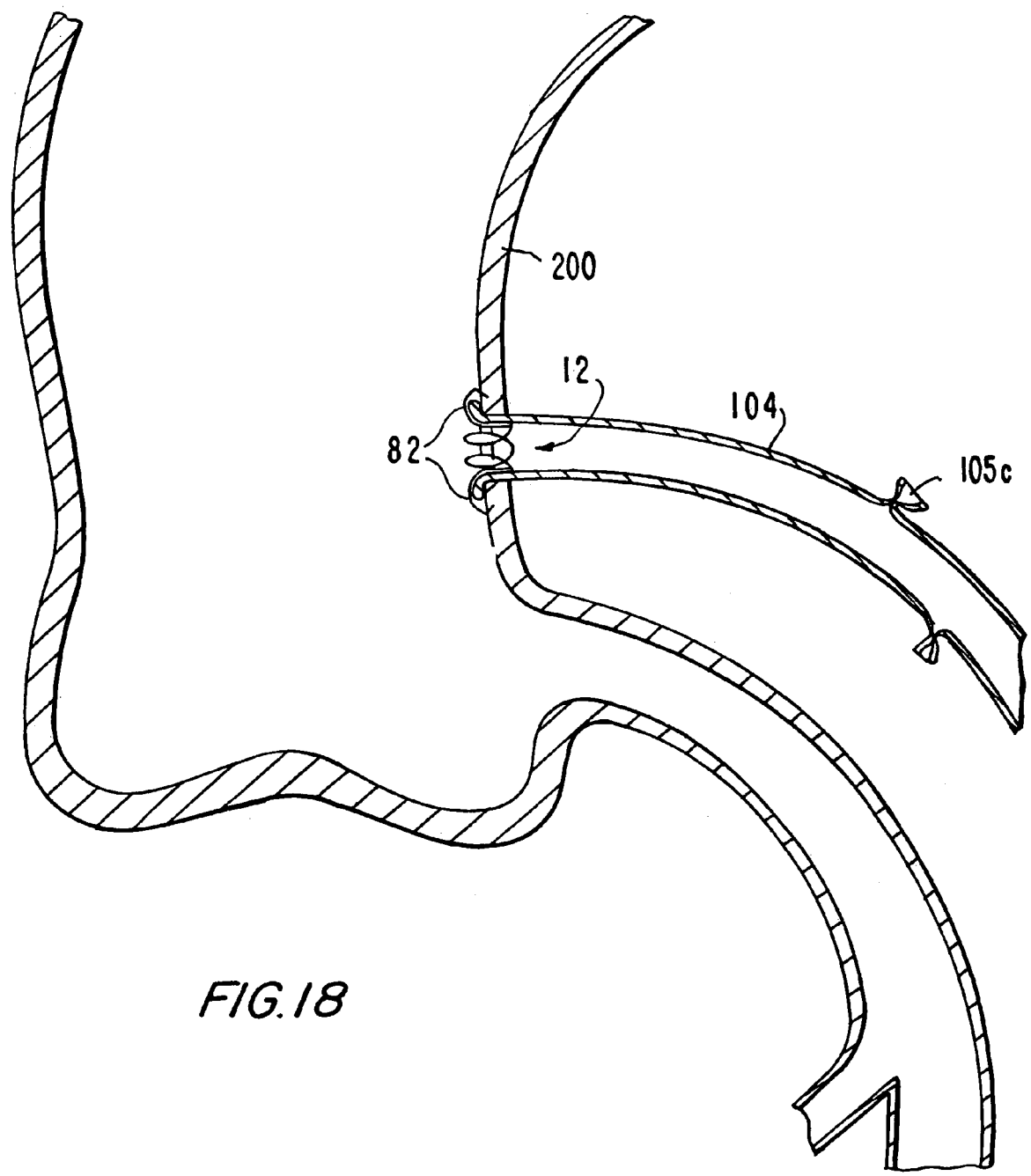
FIG. 18 is a simplified enlarged sectional view similar to FIG. 17, showing the end result of using the FIG. 1 apparatus and the FIG. 5 connector in accordance with the invention.

The proximal attachment of graft 104 to the body conduit, e.g., the aorta 200, by a connector, such as connector 12, is illustrated in FIGS. 17-18. A first step in the process may be to side-clamp the aorta 200 to allow perfusion while controlling blood loss during the deployment of the connector.

A next step in the installation of graft 104 may be to pierce conduit 200 with the sharpened end of guide wire 162. Guide wire 162 may be deployed from inside conduit 200 to the outside thereof by the use of a catheter arrangement substantially similar to catheter 152, described above with respect to FIGS. 10-11.

Graft installing apparatus 16 is inserted through the surgical access opening such that a portion of apparatus passes through side branch 105c of graft 104 to access the interior or connector 12, which is attached to the axial end portion of the graft 104. The step may be performed with the end portion of graft 104 entirely within the patient, or alternatively, while the end portion of graft 104 is extending outside of the patient through the surgical access opening.

A nose portion (not shown), similar to portion 180, described above with respect to FIGS. 13-14, may be helpful to assist in the insertion of an axial portion of connector 12 through the wall of conduit 200. Alternatively, an incision may be made in conduit 200 by a scalpel or other sharpened instrument inserted through the surgical access opening or percutaneously from the inside to the outside of the conduit 200. As described above for the installation of connector 10 (FIG. 14), members 94 of connector 12 act as "stops" in order to assist in positioning a predetermined axial portion of connector 12 in the conduit wall. Balloon 18b is expanded substantially as described above with respect to FIG. 15, in order to expand connector and make the fluid-tight connection between conduit 200 and graft 104.

Figure 19:
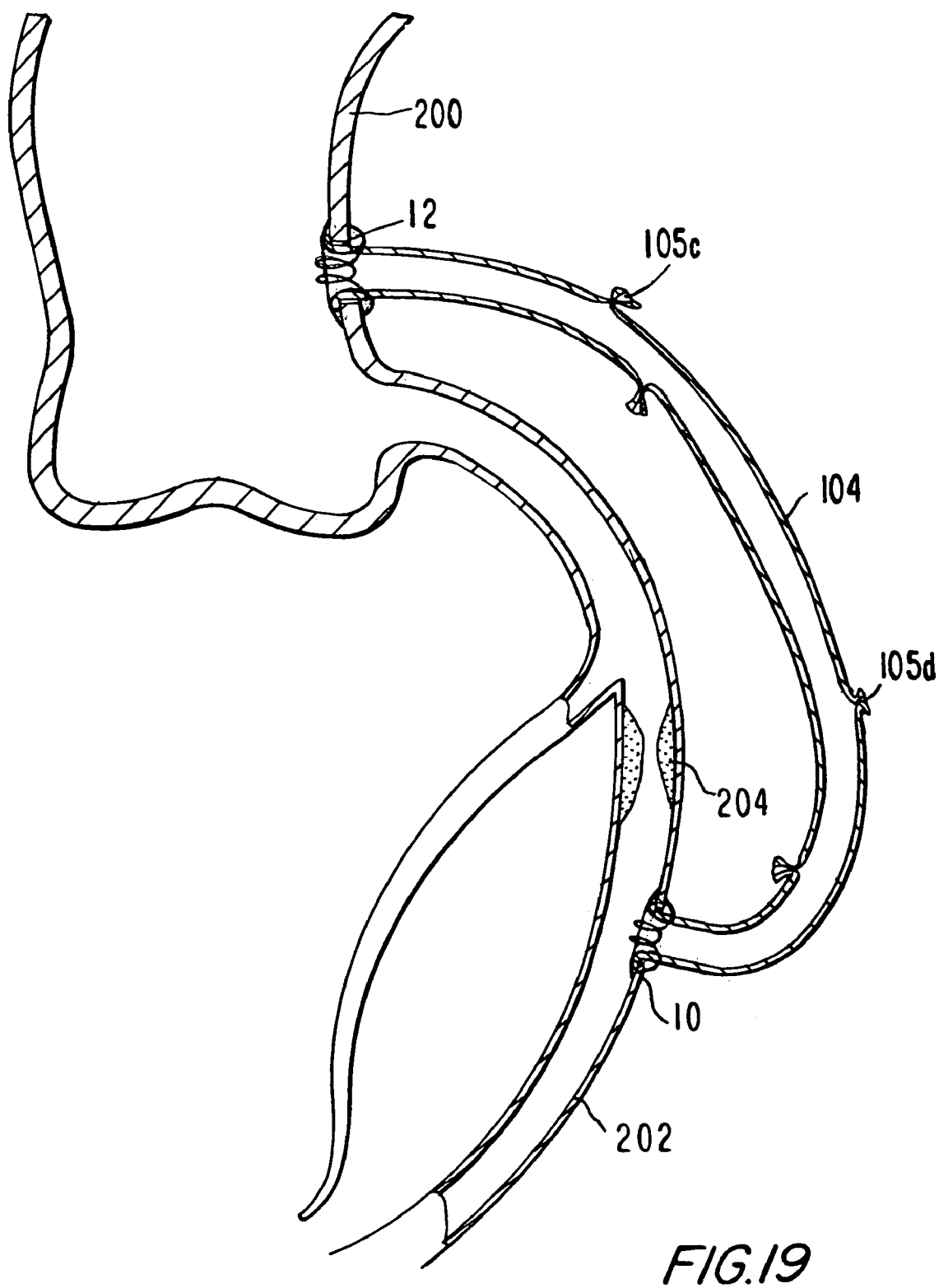
FIG. 19 is a simplified sectional view, showing the end result of using the FIG. 2 connector and the FIG. 5 connector in accordance with the invention.

As illustrated in FIG. 18, expansion of balloon 18b expands connector 12 such that the free ends of members 82 preferably penetrate the side wall of conduit 200 to further secure connector 12 and graft 104 in the aperture in the side wall. Members 67, 68, and 69 may also flare out somewhat outside the side wall of graft 200 to help ensure that graft 104 remains open where it connects to conduit 200. The balloon catheter 17b and balloon 18b are removed from the anastomosis site (e.g., by pulling out through the graft 104. Side branch, such as side branch 105c, may be closed by suturing, stapling, the application of clips, or other means known in the art. FIG. 19 illustrates the complete coronary artery bypass graft, allowing the flow of arterial blood from aorta 200, through graft 104 to supply coronary artery 202 downstream of the narrowing 204.

According to another embodiment of the present invention, the steps of installing guide member 160/162 from inside conduit 202 may be omitted. For such an alternative embodiment, guide wire 160/162 may be installed from the outside to the inside of conduits 200 and/or 202 by the use of a sharpened instrument, such as a scalpel, to make an incision in the conduit. Subsequently, the guide wire is inserted through the incision. According to yet another alternative embodiment, the guide wire may be deployed entirely percutaneously, i.e., passed along the patient's vascular system and then deployed from inside a first body conduit to the outside thereof by passing through the wall of the first conduit. The guide member is then directed to the second conduit by a steerable device, and passes through the wall of the second conduit. This is described in greater detail in Sullivan et al. U.S. Pat. No. 6,120,432, which is incorporated by reference in its entirety herein.

Figures 20, 20A:
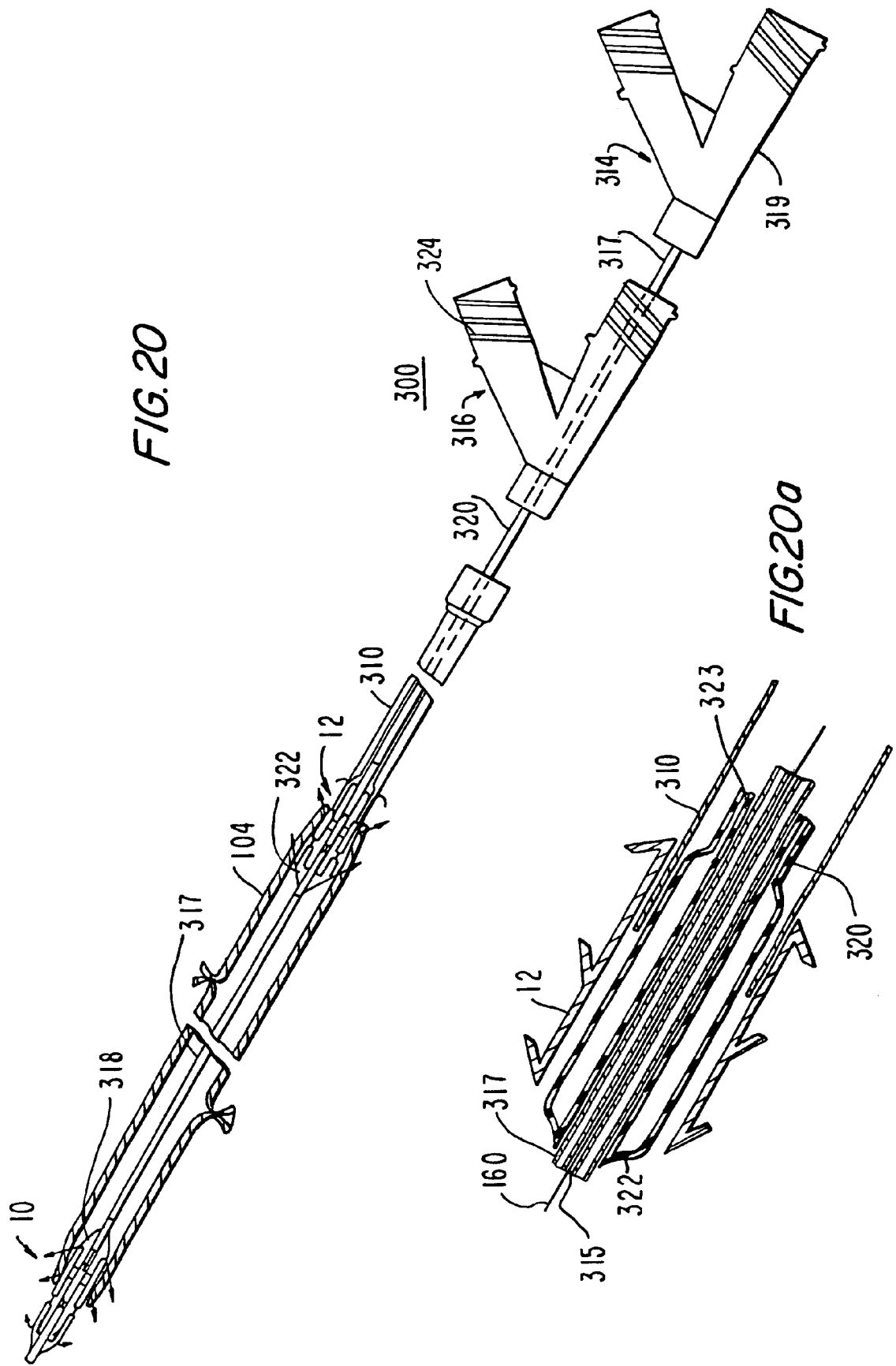
FIG. 20 is a simplified view, in partial section, of an alternative embodiment of the apparatus in accordance with the invention.
FIG. 20(a) is an enlarged sectional view of a portion of the apparatus of FIG. 20 in accordance with the invention.

An alternative embodiment of the invention is illustrated in FIG. 20. Apparatus 300 is configured to make an anastomotic connection between graft 104 and two sections of body conduit with connectors 10 and 12. Apparatus 300 may be employed percutaneously along the patient's vascular system. Alternatively, apparatus may be introduced through surgical access or deployed percutaneously and installed with assistance from instrumentation inserted through surgical access openings.

Apparatus 300 includes graft installing apparatus 314, which is useful for deploying connector 10, and graft installing apparatus 316, for installing connector 12. Apparatus 300 is substantially identical to apparatus 100, with some of the differences described herein. For example, apparatus 300 allows deployment of both connectors 10 and 12 from one axial end of the graft 104. Graft installing apparatus 314 and graft installing apparatus 316 are independently operable, as will be described in greater detail below.

Graft installing apparatus 314 includes a balloon catheter 317 having a connector expanding balloon 318 attached to the end. Balloon 318 may be remotely expanded from the proximal portion 319. As FIG. 20(a) illustrates, balloon catheter 317 (and balloon 318, not shown in FIG. 20(a)) are configured with an axial opening 315 which allows guide member 160 to pass coaxially therethrough. Graft installing apparatus 316 is substantially similar to apparatus 314. Expandable balloon 322 may be remotely expanded from a proximal portion 324 connected by a balloon catheter 320. FIG. 20(a) illustrates that balloon 322 and balloon catheter 320 are configured with an axial opening 323 which allows balloon catheter 317 to pass coaxially therethrough. The axial opening 323 allows balloon 322 and balloon 318 to be shifted axially with respect to one another, e.g., to accommodate different length graft conduits 104.

A desirable feature of structure 300 is the fact that the proximal and distal connector delivery components are independent of one another in terms of deployment controls. The distal connector delivery and deployment components are coaxially inside the proximal connector delivery and deployment components. After graft 104 has been attached to connectors 10 and 12, the space between the respectively associated portions of structure 300 can be adjusted to add or remove graft length between the connectors as needed.

FIGS. 20 and 20(a) also illustrate inflation control sleeve 310 surrounding an axial portion of balloon 322. Selective inflation of balloon 322 may be achieved, wherein the portion of balloon 322 that is exposed from sleeve 310 may expand while the portion of balloon 322 that is surrounded by sleeve 310 is restrained against expansion. This selective inflation of balloon 322 allows connector 12 to be expanded in stages, as will be described in greater detail below.

An early stage in an illustrative coronary artery bypass procedure in accordance with the invention includes the accessing the distal anastomosis location, e.g., at the coronary artery. The installation of the guide member 160 is substantially described above with respect to FIGS. 9-11, above. Thus catheter 152 and guide member 160 are illustrated in FIGS. 21-23, although it is understood that the method according to the invention may be carried out without the use of guide member 160.

A later stage in the process includes accessing the aortic end of the desired bypass around narrowing 204. (See also Berg et al. U.S. Pat. No. 6,416,527, which is incorporated by reference in its entirety herein and PCT publication No. WO 00/27312, incorporated by reference above, for additional and/or alternative apparatus and/or methods usable in the aortic access that will now be described.) Catheter or catheter-like structure 300 is introduced intraluminally into the patient's circulatory system and advanced to the aorta as shown in FIG. 21. Catheter 300 is preferably introduced into the patient at a location remote from the coronary area, e.g., into the patient's vascular system at the leg and introduced into a femoral artery.

As illustrated in FIG. 21, catheter 300 is pushed into the patient until its distal portion is adjacent the inside surface of the wall of the aorta 200 where it is desired to connect the aortic end of the bypass graft around narrowing 204. Needle catheter 302 is then pushed distally so that its sharpened distal end portion passes through the wall of aorta 200. The next step is to push the distal portion of pilot wire 304 out of the distal end of needle catheter 302.

Subsequently, cutter catheter 306 is pushed in the distal direction so that a sharpened distal end of catheter 306 makes an annular cut through the wall of aorta 200 as shown in FIG. 22. As indicated by the arrow, cutter catheter 306 may be provided with threads so that rotating the cutter catheter "pulls" the catheter distally through the wall of the aorta 200. The distal portion of cutter catheter 306 tends to follow pilot wire 304 in the space between aorta 106 and pericardial membrane (not shown) to prevent cutter catheter 306 from inadvertently cutting through the pericardial membrane. The cutter catheter shaft 306 functions as a plug through the aperture in the aorta wall that the cutter catheter has formed. This prevents blood flow from the aorta into the pericardial space. The distal portion of aortic access catheter 308 is pushed distally through the aperture in the aorta wall that the cutter catheter formed, and helps to maintain a fluid-tight seal between the aortic access catheter 308 and the aorta.

When catheter 308 is satisfactorily placed in aorta 200, the physician may withdraw catheter 306, cannula 302, and wire 304, as illustrated in FIG. 23 (see, for example, Berg et al. U.S. Pat. No. 6,013,190, which is hereby incorporated by reference herein in its entirety).

A further step is shown in FIG. 24 and involves insertion of snare structure 320 axially through the lumen of aortic access catheter 308, starting from the proximal portion of the catheter, until a distal portion of structure 320 extends from the distal end of catheter 308 into the space between artery 200 and pericardial membrane (not shown). Structure 320 is preferably steerable (at least in its distal portion), and may include optical or video components to help the physician guide the distal portion of structure 320 to the vicinity of the distal portion of catheter 152. The snare loop 322 on the distal end of wire 324 may be extended from the surrounding snare sleeve 326, as shown in FIG. 24, when the distal-most portion of sleeve 326 has reached the vicinity of catheter portion 152.

Continued distal pushing of guide member 160 causes the portion outside coronary artery 202 to pass through snare loop 322. Snare loop 322 is subsequently withdrawn into snare sleeve 326, thereby interengaging guide member 160 and snare wire 324. Snare 320 is withdrawn into aortic access catheter 308, thereby creating a single longitudinal member extending across the proposed anastomosis site. Further details are described in PCT publication No. WO 00/27312, incorporated by reference above.

Figure 25:
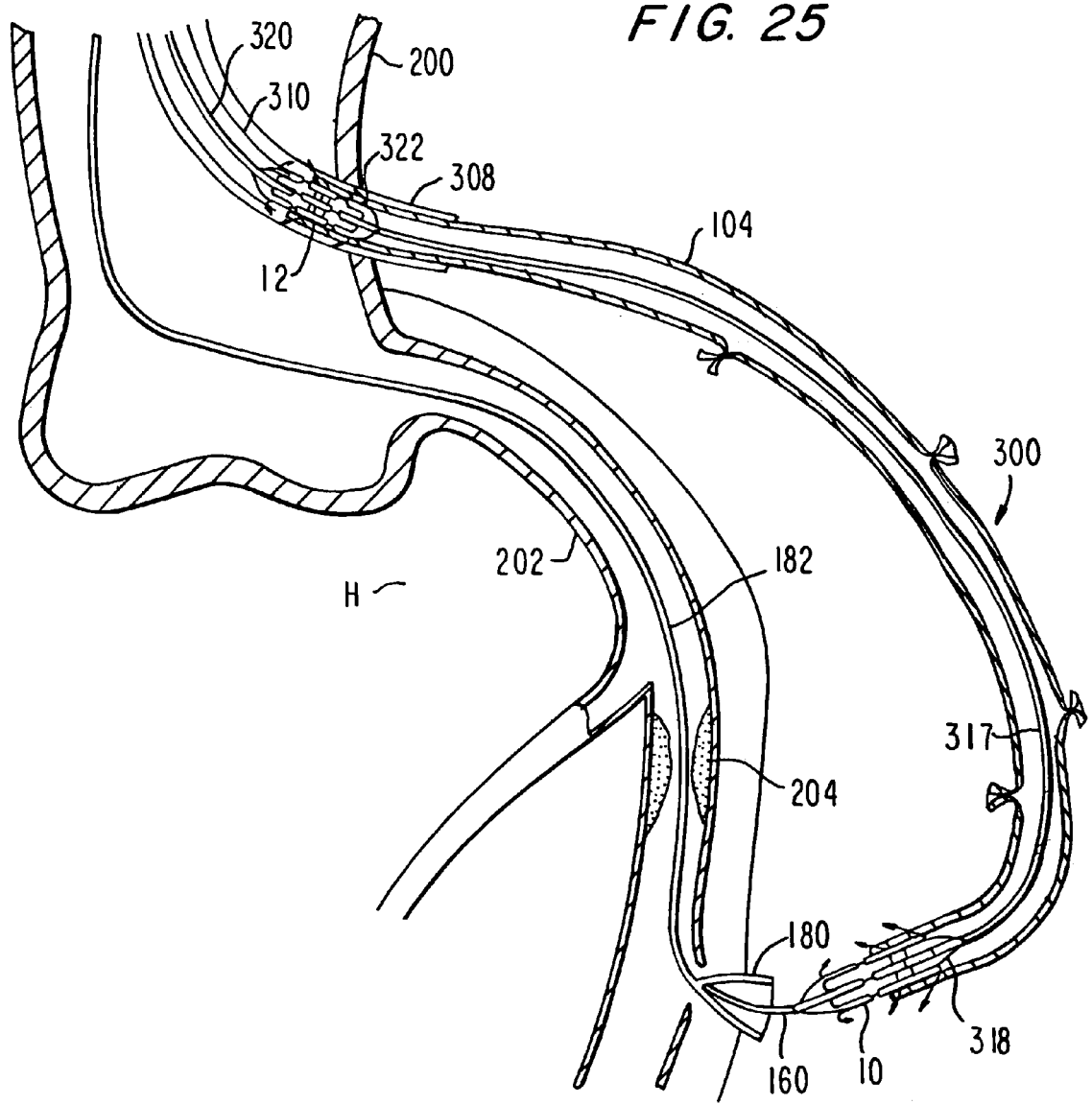
FIG. 25 is a simplified sectional view, showing an early stage in the use of the FIG. 20 apparatus, the FIG. 2 connector, and the FIG. 5 connector in accordance with the invention.

A balloon access catheter may be deployed to dilate the opening in the coronary artery substantially as described with respect to FIG. 12, above. As illustrated in FIG. 25, the distal portion of graft installing apparatus 300 is inserted along the patient's vascular system over guide member 160. According to a preferred embodiment, nose portion 180 may be advanced to dilate the coronary artery 202 at the distal anastomosis location, as illustrated in FIG. 25. The distal anastomosis is made between the graft 104 and the conduit 202, substantially as described with respect to FIGS. 13-16. For example, balloon 318, described above, is expanded to deform and deploy connector 10 substantially as described above for deforming connector 10 by expanding balloon 18a/18b. Balloon catheter 317 is configured to coaxially pass through balloon 322 and balloon catheter 320.

Figure 26:
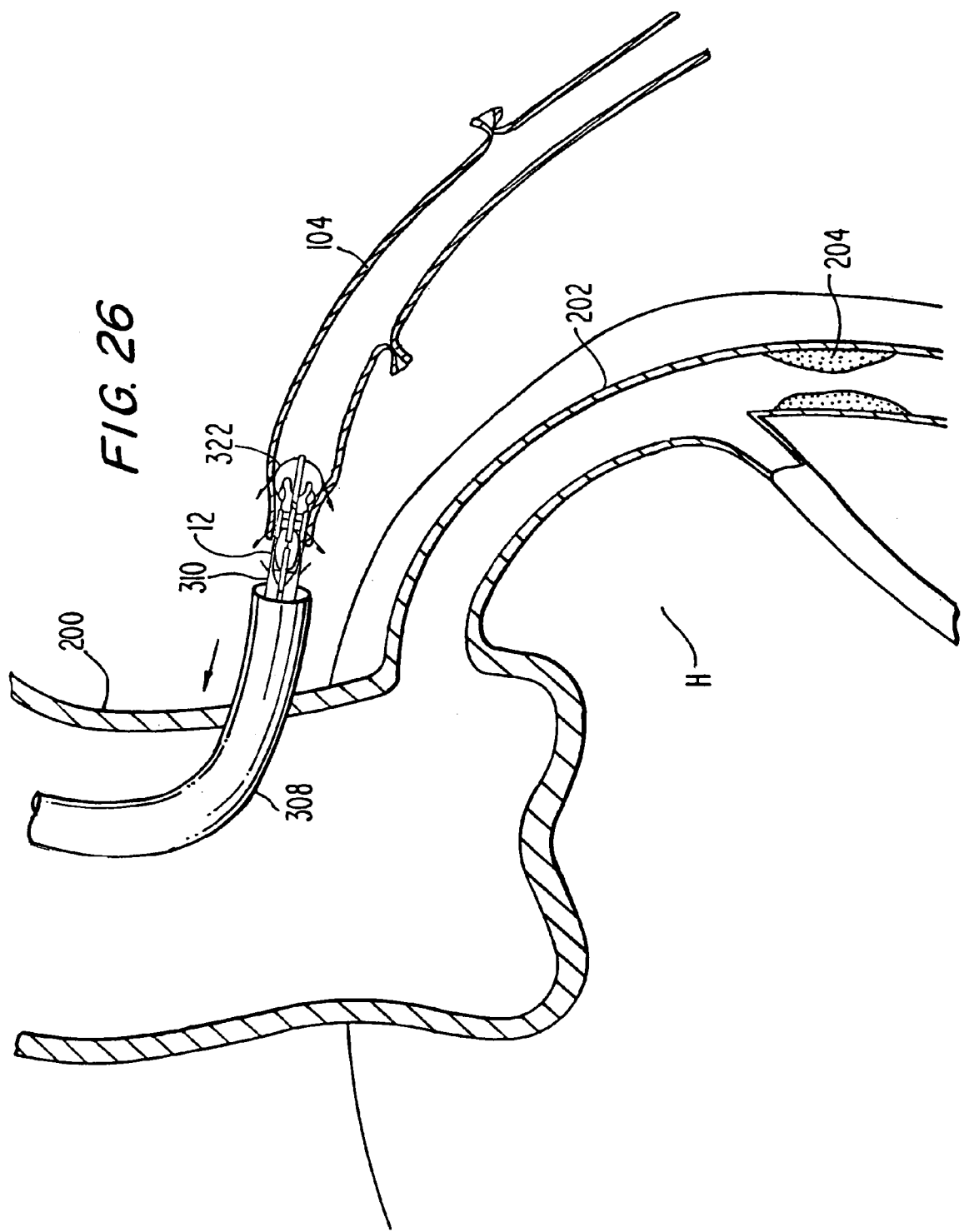
FIG. 26 is a simplified sectional view similar to FIG. 25, showing a later stage in the use of the FIG. 20 apparatus in accordance with the invention.

Graft 104, graft installing apparatus 314 and connector 12 are advanced from aortic access catheter 308, such that the connector is positioned beyond the distal end of catheter 308, as illustrated in FIG. 26. As described above, an inflation control sleeve 310 surrounds an axial portion of balloon 322 nearest aortic access catheter 308. Fluid or air is introduced into balloon 322, thereby expanding the portion of balloon 322 exposed from sleeve 310. Consequently, the proximal portion of connector 12 is expanded by balloon 322, as shown in the FIG. (The distal axial portion of balloon 322 is restrained by the inflation control sleeve and is not expanded, nor is the distal axial portion of connector 12.) The expanded proximal portion of connector 12 becomes annularly larger than the aortic access catheter 308. As indicated by the arrow, the aortic access catheter 308 and the connector 12 may be moved proximally into the aorta 200. When moved into the aperture of the aorta, the expanded proximal portion of connector 12 helps to maintain the fluid-tight seal around the aperture in the aorta, and to control blood loss.

FIG. 27 illustrates the position of the connector 12 with respect to the wall of aorta 200. The free ends 92 of connector 12 acts as "stops" to prevent the connector 12 from advancing further into the aorta 200, and therefore assist in properly positioning connector 12 with respect to the aorta 200.

Inflation control sleeve 310 is retracted into the lumen of the aorta to expose the distal portion of balloon 322. Balloon 322 is subsequently expanded (as illustrated in the FIG.), thereby annularly expanding the distal portion of the connector, as illustrated in FIG. 28. Connector 12 thus forms an anastomotic connection between graft 104 and aorta 200. The installing apparatus, such as inflation control member 310, aortic access catheter 308, and expandable member 322 are subsequently removed from the patient.

It will be understood that the foregoing is only illustrative of the principles of the invention and that various modifications can be made by those skilled in the art without departing from the scope and spirit of the invention. For example, the invention can be used to add a graft to the patient's circulatory system elsewhere than between the aorta and a coronary artery as has been specifically shown and described above. Similarly, although particular examples of connector types have been shown herein, many other forms of connectors can be used instead if desired.

What is claimed is:

1. Apparatus for making an anastomotic connection between a tubular graft conduit and a patient's tubular body structure at first and second spaced locations comprising:
   first and second connectors attached to the axial ends of the tubular graft conduit and having interior portions substantially accessible to the interior of the tubular graft conduit, a portion of the first and second connectors configured for annular expansion; and
   first installation structure having a first expandable portion for annularly expanding a portion of the first connector by engaging the interior of the first connector and a first elongated structure for remotely controlling expansion of the first expandable member, the first installation structure having an axial opening extending therethrough;
   second installation structure having a second expandable portion for annularly expanding a portion of the second connector by engaging the interior of the second connector and an second elongated structure for remotely controlling expansion of the second expandable member, a portion of the second installation structure extending coaxially through the axial opening in the first installation structure, wherein the first and second installation structures are remotely controllable from outside the patient;
   an elongated structure configured for passage into and along the inner lumen of the patient's tubular body structure to the first location, wherein the elongated structure defines an interior configured to receive the tubular graft; and
   a balloon structure for selectively enlarging an opening at the second location, the balloon structure having an internal lumen for coaxial advancement over the longitudinal member.

2. The apparatus defined in claim 1, wherein the first elongated structure and the second elongated structure extend from the same one of the first and second axial ends of the tubular graft conduit.

3. The apparatus defined in claim 1, wherein the apparatus is configured for passage into and along a inner lumen of the patient's tubular body structure.

4. The apparatus defined in claim 1, further comprising:
   a longitudinal member adapted for installation between the first and second locations,
   wherein the tubular graft is adapted for coaxial advancement over the longitudinal member between the first location and the second location.

5. The apparatus defined in claim 1, further comprising:
   a tapered sheath structure adapted for positioning about a distal portion of one of the connectors during passage of said connector and said sheath structure through the opening at the second location to assist said passage therethrough.

6. The apparatus defined in claim 5, wherein the sheath structure further comprises a tubular member extending axially from the sheath structure, wherein the sheath structure and the tubular member are configured for axial movement with respect to the longitudinal member.

7. The apparatus defined in claim 6, wherein the sheath structure and the tubular member are configured to advance distally into and along the lumen of the patient's tubular body structure after said passage through the opening at the second location.

8. The apparatus defined in claim 6, wherein the sheath structure and the tubular member are configured to advance proximally into the interior of one of the connectors following annular expansion and into and along the lumen of the tubular graft conduit after said passage through the opening at the second location.

9. The apparatus defined in claim 1, further comprising:
   a fourth elongated structure configured to annularly surround a selected axial portion of one of the expandable portions in order to selectively restrain the selected axial portion of the expandable portion from expansion, thereby controlling selective expansion of one of the connectors.

* * * * *